US009040676B2

(12) United States Patent
Phillips et al.

(10) Patent No.: US 9,040,676 B2
(45) Date of Patent: May 26, 2015

(54) VIGILANT CELLS

(75) Inventors: M. Ian Phillips, Tampa, FL (US); Yao Liang Tang, St. Petersburg, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 1769 days.

(21) Appl. No.: 10/567,298

(22) PCT Filed: Aug. 11, 2004

(86) PCT No.: PCT/US2004/026195
§ 371 (c)(1),
(2), (4) Date: Dec. 18, 2006

(87) PCT Pub. No.: WO2005/017164
PCT Pub. Date: Feb. 24, 2005

(65) Prior Publication Data
US 2007/0117766 A1 May 24, 2007

Related U.S. Application Data

(60) Provisional application No. 60/494,184, filed on Aug. 11, 2003, provisional application No. 60/494,185, filed on Aug. 11, 2003, provisional application No. 60/513,067, filed on Oct. 21, 2003, provisional application No. 60/513,657, filed on Oct. 23, 2003.

(51) Int. Cl.
| | |
|---|---|
| C07H 21/00 | (2006.01) |
| C07H 21/04 | (2006.01) |
| C07H 21/02 | (2006.01) |
| C12P 21/06 | (2006.01) |
| C12N 7/00 | (2006.01) |
| C12N 7/01 | (2006.01) |
| C12N 15/00 | (2006.01) |
| A61K 48/00 | (2006.01) |
| C12N 15/85 | (2006.01) |
| C12N 15/86 | (2006.01) |
| C12N 5/0775 | (2010.01) |
| A61K 35/12 | (2006.01) |

(52) U.S. Cl.
CPC ....... *A61K 48/0058* (2013.01); *A61K 2035/124* (2013.01); *C12N 15/85* (2013.01); *C12N 15/86* (2013.01); *C12N 2510/02* (2013.01); *C12N 2750/14143* (2013.01); *C12N 2800/00* (2013.01); *C12N 2830/002* (2013.01); *C12N 2830/008* (2013.01); *C12N 2830/85* (2013.01); *C12N 5/0663* (2013.01)

(58) Field of Classification Search
None
See application file for complete search history.

(56) References Cited

FOREIGN PATENT DOCUMENTS

| | | |
|---|---|---|
| WO | WO 00/50048 A3 | 8/2000 |
| WO | WO 2004/024867 A2 | 3/2004 |
| WO | WO 2005/017165 A1 | 2/2005 |

OTHER PUBLICATIONS

Fields et al., A novel genetic system to detect protein-protein interactions, Nature, 340(6230):245-6, 1989.*
Juan et al, Adenovirus-mediated heme oxygenase-1 gene transfer inhibits the development of atherosclerosis in apolipoprotein E-deficient mice, Circulation. Sep. 25, 2001;104(13):1519-25,2001.*
Nicklin et al., Tropism-modified adenoviral and adeno-associated viral vectors for gene therapy, Curr Gene Ther. 2(3):273-93, 2002.*
Turgeman et al., Engineered human mesenchymal stem cells: a novel platform for skeletal cell mediated gene therapy. J Gene Med. 3(3):240-51, 2001.*
Fukuda et al., Regeneration of cardiomyocytes from bone marrow: Use of mesenchymal stem cell for cardiovascular tissue engineering, Cytotechnology 41(2-3):165-75, 2003.*
Fukuda et al., Regeneration of cardiomyocytes from bone marrow: Use of mesenchymal stem cell for cardiovascular tissue engineering, Cytotechnology 41(2-3):165-175, 2003.*
Nathwani et al., Efficient gene transfer into human cord blood CD34+ cells and the CD34+CD38-subset using highly purified recombinant adeno-associated viral vector preparations that are free of helper virus and wild-type AAV, Gene Ther. 7(3):183-95, 2000.*
Zhang (Mar. 2001,J Mol Cell Cardiol;, 33:907-921.*
Francis (2001, Physiol Genomics,7:79-94.*
U.S. Appl. No. 10/567,275, filed Feb. 6, 2006, Phillips et al.
Abruzzese, R. et al. "Ligand-dependent regulation of vascular endothelial growth factor and erythropoietin expression by a plasmid-based autoinducible GeneSwitch system" *Mol. Therapy*, 2000, 2:276-287.
Chen, H. et al. "Protection against ischemia-reperfusion injury and myocardial dysfunction by antisense-oligodeoxynucleotide by antisense-oligodeoxynucleotide directed at angiotensin-converting enzyme mRNA" *Gene Ther.*, 2001, 8:804-810.
Chen, H. et al. "Protection against myocardial dysfunction induced by global ischemia-reperfusion by antisense-oligodeoxynucleotides directed by $\beta_1$-adrenoceptor mRNA" *J. Pharmacol. Exp. Ther.*, 2000, 294:722-727.
Conget, P.A. and Minguell, J.J. "Adenoviral-mediated gene transfer into ex vivo expanded human bone marrow mesenchymal progenitor cells" *Exp. Hematol*, 2000, 28:382-390.

(Continued)

Primary Examiner — Valarie Bertoglio
(74) Attorney, Agent, or Firm — Saliwanchik, Lloyd & Eisenschenk

(57) ABSTRACT

The invention concerns a system for modulating tissue physiology, for example, to prevent or reverse tissue damage caused by disease. The system utilizes vigilant cells that include stable vectors containing a gene switch/biosensor and a gene amplification system. The vectors allow expression of a transgene (such as a cardioprotective gene) in the vigilant cells to be regulated in response to a physiological signal, to be switched on or off, and to provide sufficient levels of the transgene product to achieve a desired result, e.g., prevention or reversal of myocardial cell damage. In addition to myocardial infarction, the vectors can be used to treat cells in a number of other disease states, including diabetes, cancer, stroke, and atherosclerosis. These approaches to stem cell-based gene therapy provide a novel strategy not only for treatment but for prevention of cell destruction.

16 Claims, 27 Drawing Sheets

(56) References Cited

OTHER PUBLICATIONS

Davani, S. et al. "Mesenchymal progenitor cells differentiate into an endothelial phenotype, enhance vascular density, and improve heart function in a rat cellular cardiomyoplasty model" *Circulation*, 2003, 108(Suppl. 1):II253-II258.

Franz, W.M. et al. "Heart-specific targeting of firefly luciferase by the myosin light chain-2 promoter and developmental regulation in transgenic mice" *Circ. Res.*, 1993, 73:629-638.

Giniger, E. et al. "Specific DNA binding of GAL4, a positive regulatory protein of yeast" *Cell*, 1985, 40:767-774.

Gu, J. et al. "Tumor-specific transgene expression from the human telomerase reverse transcriptase promoter enables targeting of the therapeutic effects of the Bax gene to cancers" *Cancer Res.*, 2000, 60:5359-5364.

Haberman, R. et al. "Inducible long-term gene expression in brain with adeno-associated virus gene transfer" *Gene Therapy*, 1998, 5:1604-1611.

Halaby, I. et al. "Glucocorticoid-regulated VEGF expression in ischemic skeletal muscle" *Mol. Therapy*, 2002, 5:300-306.

Huang, L.E. et al. "Regulation of hypoxia-inducible factor 1α is mediated by an $O_2$-dependent degradation domain via the ubiquitin-proteasome pathway" *Proc Natl Acad Sci USA*, 1998, 95:7987-7992.

Kagiyama, T. et al. "Expression of angiotensin type 1 and 2 receptors in brain after transient middle cerebral artery occlusion in rats" *Regul. Pept.*, 2003, 110:241-247.

Keegan, L. et al. "Separation of DNA binding from the transcription-activating function of a eukaryotic regulatory protein" *Science*, 1986, 231:699-704.

Kimura, B. et al. "Attenuation of hypertension and heart hypertrophy by adeno-associated virus delivering angiotensinogen antisense" *Hypertension*, 2001, 37:376-380.

Kircheis, R. et al. "Polyethylenimine/DNA complexes shielded by transferring target gene expression to tumors after systemic application" *Gene Ther.*, 2001, 8:28-40.

Koh, G.Y. et al. "Targeted expression of transforming growth factor-β1 in intracardiac grafts promotes vascular endothelial cell DNA synthesis" *J. Clin. Invest*, 1995, 95:114-121.

Kollet, O. et al. "HGF, SDF-1, and MMP-9 are involved in stress-induced human $CD34^+$ stem cell recruitment to the liver" *J. Clin. Invest*, 2003, 112:160-169.

Mangi, A.A. et al. "Mesenchymal stem cells modified with Akt prevent remodeling and restore performance of infracted hearts" *Nat. Med.*, 2003, 9:1195-1201.

Melo, L. et al. "Gene therapy strategy for long-term myocardial protection using adeno-associated virus-mediated delivery of heme oxygenase gene" *Circulation*, 2002, 105:602-607.

Ogris, M. et al. "The size of DNA/transferring-PEI complexes is an important factor for gene expression in cultured cells" *Gene Ther.*, 1998, 5:1425-1433.

Phillips, M.I. "Gene therapy for hypertension: Antisense inhibition with adeno-associated viral vector delivery targeting angiotensin II type 1 receptor messenger ribonucleic acid" *Am. J. Cardiol.*, 1998, 82(10A):60S-62S.

Phillips, M.I. "Somatic gene therapy for hypertension" *Braz. J. Med. Biol. Res.*, 2000, 33:715-721.

Phillips, M.I. "Is gene therapy for hypertension possible?" *Hypertension*, 1999, 33:8-13.

Phillips, M.I. "Gene therapy for hypertension: The preclinical data" *Hypertension*, 2001, 38(3 Pt 2):543-548.

Phillips, M.I. "Gene therapy for hypertension: sense and antisense strategies" *Expert. Opin. Biol. Ther.*, 2001, 1(4):655-662, abstract.

Phillips, M.I. et al. "Vigilant vector: Heart-specific promoter in an adeno-associated virus vector for cardioprotection" *Hypertension*, 2002, 39(2 Pt 2):651-655.

Phillips, M.I. "Gene therapy for hypertension: The preclinical data" *Methods Enzymol.*, 2002, 346:3-13.

Ponnazhagan, S. et al. "Adeno-associated virus type 2-mediated transduction of murine hematopoietic cells with long-term repopulating ability and sustained expression of a human globin gene in vivo" *J. Virology*, 1997, 71:3098-3104.

Qiao, J. et al. "Tumor-specific transcriptional targeting of suicide gene therapy" *Gene Therapy*, 2002, 9:168-175.

Ruan, H. et al. "A hypoxia-regulated adeno-associated virus vector for cancer-specific gene therapy" *Neoplasia*, 2001, 3:255-263.

Schmitz, M.L. and Baeuerle, P.A. "The p65 subunit is responsible for the strong transcription activating potential of NF-κB" *EMBO J.*, 1991, 10:3805-3817.

Semenza, G.L. et al. "Hypoxia response elements in the aldolase A, enolase 1, and lactate dehydrogenase A gene promoters contain essential binding sites for hypoxia-inducible factor 1" *J Biol Chem.*, 1996, 271:32529-32537.

Shake, J.G. et al. "Mesenchymal stem cell implantation in a swine myocardial infarct model: engraftment and functional effects" *Ann. Thorac. Surg.*, 2002, 73:1919-1926.

Sirtori, C.R. "New targets for lipid lowering and atherosclerosis prevention" *Pharmacol Ther.*, 1995, 67:433-447.

Smith-Arica, J.R. et al. "Switching on and off transgene expression within lactotrophic cells in the anterior pituitary gland in vivo" *Endocrinology*, 2001, 142:2521-2532.

Strauer, B.E. and Kornowski, R. "Stem cell therapy in perspective" *Circulation*, 2003, 107:929-934.

Tang, X. et al. "Intravenous angiotensinogen antisense in AAV-based vector decreases hypertension" *Am. J. Physiol.*, 1999, 277(6 Pt 2):H2392-H2399.

Tang, Y.L. et al. "Paracrine action enhances the effects of autologous mesenchymal stem cell transplantation on vascular regeneration in rat model of myocardial infarction" *Ann Thorac. Surg.*, 2005, 80:229-237.

Tang, Y.L. et al. "A hypoxia-inducible vigilant vector system for activating therapeutic genes in ischemia" *Gene Ther.*, 2005, 12:1163-1170.

Tang, Y. et al. "Hypoxia inducible double plasmid system for myocardial ischemia gene therapy" *Hypertension*, 2002, 39(2 Pt 2):695-698.

Tang, Y.L. et al. "Protection from ischemic heart injury by a vigilant heme oxygenase-1 plasmid system" *Hypertension*, 2004, 43:746-751.

Tang, Y.L. et al. "Improved graft mesenchymal stem cell survival in ischemic heart with a hypoxia-regulated heme oxygenase-1 vector" *J. Am. Coll. Cardiol.*, 2005, 46:1339-1350.

Tang, Y.L. et al. "A vigilant, hypoxia-regulated heme oxygenase-1 gene vector in the heart limits cardiac injury after ischemia-reperfusion in vivo" *J. Cardiovasc. Pharmacol. Ther.*, 2005, 10:251-263.

Tang, Y. et al. "Vigilant vectors: adeno-associated virus with a biosensor to switch on amplified therapeutic genes in specific tissues in life-threatening disease" *Methods*, 2002, 28:259-266.

Tang, Y.L. et al. "Autologous mesenchymal stem cell transplantation induce VEGF and neovascularization in ischemic myocardium" *Regul. Pept.*, 2004, 117:3-10.

Tang, Y.L. et al. "Mobilizing of haematopoietic stem cells to ischemic myocardium by plasmid mediated stromal-cell-derived factor-1α (SDF-1α) treatment" *Regul. Pept.*, 2005, 125:1-8.

Woo, Y.J. et al. "Recombinant adenovirus-mediated cardiac gene transfer of superoxide dismutase and catalase attenuates postischemic contractile dysfunction" *Circulation*, 1998, 98:II255-II261.

Wu, P. et al. "Adeno-associated virus vector-mediated transgene integration into neurons and other nondividing cell targets" *J. Virol.*, 1998, 72:5919-5926.

Yamaguchi, J. et al. "Stromal cell-derived factor-1 effects on ex vivo expanded endothelial progenitor cell recruitment for ischemic neovascularization" *Circulation*, 2003, 107:1322-1328.

Yang, B.C. et al. "Critical role of AT1 receptor expression after ischemia/reperfusion in isolated rat hearts: Beneficial effect of antisense oligodeoxynucleotides directed at AT1 receptor mRNA" *Circ. Res.*, 1998, 83:552-559.

Yang, B.C. et al. "Increase in angiotensin II type 1 receptor expression immediately after ischemia-reperfusion in isolated rat hearts" *Circulation*, 1997, 96:922-926.

Zvaritch, E. et al. "The transgenic expression of highly inhibitory monomeric forms of phospholamban in mouse heart impairs cardiac contractility" *J. Biol. Chem.*, 2000, 275:14985-14991.

\* cited by examiner rAAV-GS-ODD rAAV-Gene-hHO-1

FIG. 3A
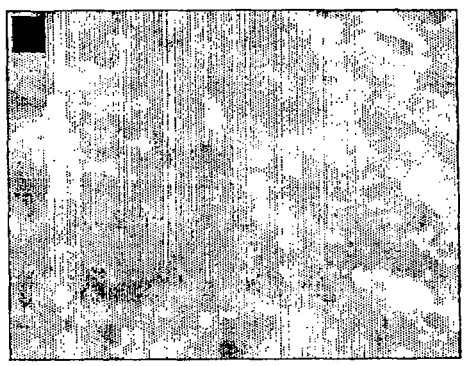
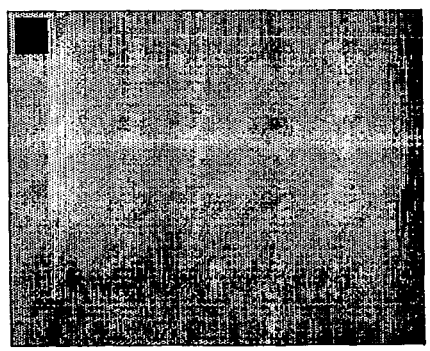
FIG. 3B           FIG. 3C

VIGILANT CELLS

CROSS-REFERENCE TO RELATED APPLICATIONS

The present application is the National Stage of International Application Number PCT/US2004/026195, filed Aug. 11, 2004, which claims the benefit of U.S. Provisional Application Ser. No. 60/513,657, filed Oct. 23, 2003, U.S. Provisional Application Ser. No. 60/494,185, filed Aug. 11, 2003, U.S. Provisional Application Ser. No. 60/513,067, filed Oct. 21, 2003, and U.S. Provisional Application Ser. No. 60/494,184, filed Aug. 11, 2003, each of which are hereby incorporated by reference herein in their entirety, including any figures, tables, nucleic acid sequences, amino acid sequences, and drawings.

GOVERNMENT SUPPORT

The subject matter of this application has been supported by a research grant from the National Institutes of Health under grant number 5R37HL2733423. Accordingly, the government may have has certain rights in this invention.

BACKGROUND OF THE INVENTION

Stem cell-based therapies are being explored for the treatment of several disease states characterized by damaged tissue. Although stem cells injected into damaged tissue have been shown to at least partially regenerate the tissue, the delivered cells and/or regenerated tissue are subsequently destroyed by the underlying cause of the disease. The development of methods for enhancing the survival of transplanted stem cells/regenerated tissue would therefore be useful for the successful implementation of stem cell regenerative therapy.

Life-threatening and chronic diseases are often characterized by the presence of particular physiological signals. For example, hypoxia is a signal associated with ischemic heart disease, while high blood glucose is a signal for diabetes. Such disease-associated signals directly or indirectly modulate gene expression in cells exposed to the signals. If these signals could be harnessed to activate expression of therapeutic or protective gene products, the success of the stem cell-based therapy might be improved. For example, when engrafted into a heart, stem cells that sense and respond to hypoxia by expressing a cardioprotective gene that promotes the long-term survival of the transplanted stem cells and surrounding tissue in the pathologic (hypoxic) environment would be useful for treating cardiac infarction or for preventing pathology due to cardiac ischemia.

BRIEF SUMMARY OF THE INVENTION

The invention relates to the fields of biology, gene therapy, cell therapy and medicine. More particularly, the invention relates to compositions and methods for modifying a tissue by delivering to the tissue cells that have been engineered to express protective or therapeutic genes in response to a particular stimulus.

A system for modulating tissue physiology has been developed. The system employs genetically manipulated "vigilant cells", that are useful for improving the survival of such cells as well as other cells in a locally pathologic (e.g. hypoxic) environment. Integrated within the genomes of vigilant cells are stable vectors containing a gene switch/biosensor and a gene amplification system to prevent or reverse tissue damage caused by disease. Grafted vigilant cells modified in this manner might more efficiently supplement the function of weakened regenerated tissue compared to non-vigilant cells (i.e., cells lacking a gene switch/biosensor and a gene amplification system) because the vectors allow transgene (e.g., a protective gene) expression in the regenerated tissue from vigilant cells to be regulated (e.g., switched on or off) in response to a physiological signal, and to provide sufficient levels of the transgene product to effect a desired result, e.g., prevention or reversal of cell damage. Multiple protective genes can be delivered simultaneously by the invention in response to a single stimulus to, for example, prevent or reverse tissue damage caused by disease.

While the system of the invention may be used in a number of different applications (as treatment or prophylaxis for diseases such as diabetes, cancer, stroke, pulmonary fibrosis, arthritis, atherosclerosis and inflammation), one application utilizes cells that include a dual rAAV vector system to detect and respond to hypoxia in cardiac tissue. The first rAAV vector in the system is the "sensor" vector. This vector contains a promoter linked to a sequence encoding an oxygen-sensitive chimeric transactivator, which is termed a redox sensor toggle (RST). The redox refers to reduced oxygen availability and the toggle refers to the ability of the system to switch on genes. The RST contains a GAL4 DNA-binding domain (DBD), an oxygen-dependent degradation domain (ODD), and a p65 activation domain (p65 AD). The second rAAV vector is the "effector" vector which contains a cardioprotective gene linked to a GAL4 upstream activating sequence (UAS). The sensor rAAV vector expresses the chimeric transactivator specifically in the heart. In response to hypoxia, the transactivator binds to the GAL4 UAS sequence in the effector rAAV vector, resulting in the expression of the cardioprotective gene. Vigilant cells can thus be delivered to the myocardium as a way of preventing or reversing tissue damage associated with hypoxia.

The vigilant cells of the invention and methods of their use exhibit many advantageous characteristics. Importantly, the vigilant cell system is an on/off system that can be regulated by a signal related to a pathologic condition (e.g. hypoxia associated with ischemia). The system is also advantageous in that it can be used to treat or prevent a wide variety of different disease states. In addition, the system allows the use of naturally occurring transgenes which permits it to function in a way that more closely resembles the physiological condition than other systems and also reduces the chance that an adverse event (e.g. tumor formation) might occur. The vigilant cells can also be used to induce an anti-apoptotic effect in treated tissues.

Unless otherwise defined, all technical terms used herein have the same meaning as commonly understood by one of ordinary skill in the art to which this invention belongs. Commonly understood definitions of molecular biology terms can be found in Rieger et al. Glossary of Genetics: Classical and Molecular, 5th edition, Springer-Verlag: New York, 1991; and Lewin, Genes V, Oxford University Press: New York, 1994. Commonly understood definitions of virology terms can be found in Granoff and Webster, Encyclopedia of Virology, 2nd edition, Academic Press: San Diego, Calif., 1999; and Tidona and Darai, The Springer Index of Viruses, 1st edition, Springer-Verlag: New York, 2002. Commonly understood definitions of microbiology can be found in Singleton and Sainsbury, Dictionary of Microbiology and Molecular Biology, 3rd edition, John Wiley & Sons: New York, 2002.

Although methods and materials similar or equivalent to those described herein can be used in the practice or testing of the present invention, suitable methods and materials are described below. All publications, patent applications, patents and other references mentioned herein are incorporated by reference in their entirety. In the case of conflict, the present specification, including definitions will control. The particular embodiments discussed below are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3C are photomicrographs showing vigilant cells expressing hHO-1 in ischemic myocardium after cell transplantation. Surviving vigilant cells were identified by DAPI-labeled nuclei (FIG. 3B), hHO-1 expression (TRITC) (FIG. 3C), and both DAPI and TRITC staining (FIG. 3A).

FIGS. 8A-8C: 4',6-diamidino-2'-phenylindole (DAPI); FIGS. 8D-F: TUNEL; and FIGS. 8G-8I: hHO-1.

FIGS. 10-10C show cells of groups $MSC_{VHO-1}$, $MSC_{VlacZ}$, and MSCs, respectively, labeled with 4',6-diamidino-2'-phenylindole (DAPI).

FIGS. 11A-11C show implanted cells of the $MSC_{VHO-1}$ group, $MSC_{VlacZ}$, and MSC group, respectively, labeled with DAPI. FIGS. 11D-11F show hHO-1 staining in implanted cells of the $MSC_{VHO-1}$ group, $MSC_{VlacZ}$, and MSC group, respectively. FIGS. 11G-11I: Merge.

FIG. 12A: $MSC_{VHO1}$; FIG. 12B: $MSC_{VlacZ}$; FIG. 12C: MSCs; and FIG. 12D: medium.

DETAILED DESCRIPTION OF THE INVENTION

Figure 1:
FIG. 1 is a schematic depiction of two plasmid constructs used in the invention.
Figure 1:
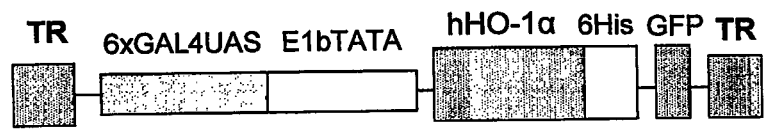

The invention provides a system for modulating tissue physiology to, for example, prevent or reverse tissue damage caused by disease. The system utilizes cells that include stable vectors containing a gene switch/biosensor and a gene amplification system. The vectors allow transgene (e.g., cardioprotective gene) expression in the vigilant cells to be regulated in response to a physiological signal, to be switched on or off, and to provide sufficient levels of the trans-gene product to effect a desired result, e.g., prevention or reversal of cell damage. Multiple protective genes can be delivered simultaneously by the invention in response to a single stimulus. The vigilant cells can be delivered to a site of damaged tissue such as an infarct or to the site of tissue that might become damaged, e.g., myocardium in a patient at high risk for a myocardial infarction (MI). The below described preferred embodiments illustrate adaptations of these compositions and methods. Nonetheless, from the description of these embodiments, other aspects of the invention can be made and/or practiced based on the description provided below.

Biological Methods.

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992. Conventional methods of gene transfer and gene therapy can also be adapted for use in the present invention. See, e.g., Gene Therapy Methods: ed. M. I. Phillips, Vol. 436, Methods in Enzymology, Academic Press, 2002; Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996.

Cells.

Vectors containing a gene switch/biosensor and a gene amplification system might be introduced into a number of different cell types depending on the particular application of the invention. For example, cells (e.g. muscle cells such as cardiomyocytes, hepatocytes, tubular cells in kidney, type I and II pneumocytes in lung, ependymal cells and cells from the subventricular zone in central nervous system, blood cells such as B cells or T cells, and duct cells in pancreas, epidermal cells in skin, endothelial cells, fat cells, epithelial cells, neurocells, Schwann cells, and so forth) from a target tissue in an animal subject may be isolated from the subject, processed ex vivo to introduce the gene switch/biosensor and gene amplification system, and then delivered back to the target tissue in the subject. Because of their developmental plasticity, preferred cells for use in the invention are pluripotent or totipotent stem cells. Such stem cells may be embryonic (see, e.g., U.S. Pat. Nos. 5,843,780 and 6,200,806), neonatal, or from an adult animal. For transplantation into a subject, to avoid immune system-mediated rejection, cells of the invention are preferably histocompatible with the host subject.

For delivery to cardiac tissue, the use of hematopoietic stem cells and mesenchymal stem cells is preferred as these cells have been shown to differentiate into functional cardiomyocytes when in the presence of differentiated cardiomyocytes. See Orlic et al., Nature 410:701-705, 2001; and Condorelli et al., Proc. Nat'l. Acad. Sci. USA 98:10733-10738, 2001. MSC are particularly suited as a delivery vehicle for gene transfer. MSC can be obtained from a bone marrow aspirate taken from the iliac crest of adult animals (e.g., human subjects) and are well tolerated when transplanted to a host animal. MSC can be ex vivo expanded to large numbers and retain the ability to differentiate into cardiac, bone, adipocytes and muscle cells in vitro and in vivo. Mosca et al., Clin. Orthop. 379 Suppl: S71-90, 2000; and Le Blanc, K., Lakartidningen 99:1318-1324, 2002. Muscle-derived stem cells (MDSCs) are also capable of delivering therapeutic genes and differentiating into a cardiomyocyte lineage within the heart. MDSCs are easily accessible via simple biopsy of the patient's own muscle. The isolation and characteristics of MDSCs and their use in regenerative medicine are reviewed in Sakai et al., Trends Cardiovasc. Med. 12:115-120, 2002. Based on their differentiation properties and facility of ex vivo expansion, human bone marrow mesenchymal progenitor cells (MPC) are also a suitable vehicle for delivering therapeutic genes to the bone marrow and other mesenchymal tissues. For example, MPC can be expanded ex vivo and infected with a rAAV virion of the invention or transduced with a stimulus-responsive rAAV vector(s). Conget et al., Exp. Hematol. 28:382-390, 2000.

Cells genetically modified with the vectors of the invention can range in plasticity from totipotent or pluripotent stem cells (e.g., adult or embryonic), precursor or progenitor cells, to highly specialized cells, such as those of the central nervous system (e.g., neurons and glia), pancreas, heart, lung, and liver. Stem cells can be obtained from a variety of sources, including embryonic tissue, fetal tissue, adult tissue, umbilical cord blood, peripheral blood, bone marrow, and brain, for example. Methods and markers commonly used to identify stem cells and to characterize differentiated cell types are described in the scientific literature (e.g., Stem Cells: Scientific Progress and Future Research Directions, Appendix E1-E5, report prepared by the National Institutes of Health, June, 2001). The list of adult tissues reported to contain stem cells is growing and includes bone marrow, peripheral blood, umbilical cord blood, brain, spinal cord, dental pulp, blood vessels, skeletal muscle, epithelia of the skin and digestive system, cornea, retina, liver, and pancreas.

There are over 200 cell types in the human body, and the vectors of the subject invention can be introduced into any of them. A non-exhaustive list of cell types within into which vectors containing a gene switch/biosensor and a gene amplification system may be introduced is shown in Table 1. Other examples of cell types that can be genetically modified with the vectors of the invention include those disclosed by Spier R. E. et al., eds., (2000) The Encyclopedia of Cell Technology, John Wiley & Sons, Inc., and Alberts B. et al., eds., (1994) Molecular Biology of the Cell, 3$^{rd}$ ed., Garland Publishing, Inc., e.g., pages 1188-1189.

TABLE 1

Examples of Target Cells

Keratinizing Epithelial Cells keratinocyte of epidermis
basal cell of epidermis
keratinocyte of fingernails and toenails
basal cell of nail bed
hair shaft cells
   medullary
   cortical
   cuticular
hair-root sheath cells
   cuticular
   of Huxley's layer
   of Henle's layer
   external
hair matrix cell
Cells of Wet Stratified Barrier Epithelia surface epithelial cell of stratified squamous epithelium of
cornea tongue, oral cavity,
esophagus, anal canal, distal urethra, vagina
basal cell of these epithelia
cell of urinary epithelium
Epithelial Cells Specialized for Exocrine Secretion cells of salivary gland
   mucous cell
   serous cell
cell of von Ebner's gland in tongue
cell of mammary gland, secreting milk
cell of lacrimal gland, secreting tears
cell of ceruminous gland of ear, secreting wax
cell of eccrine sweat gland, secreting glycoproteins
cell of eccrine sweat gland, secreting small molecules
cell of apocrine sweat gland
cell of gland of Moll in eyelid
cell of sebaceous gland, secreting lipid-rich sebum
cell of Bowman's gland in nose
cell of Brunner's gland in duodenum, secreting alkaline solution
of mucus and enzymes
cell of seminal vesicle, secreting components of seminal fluid,
including fructose
cell of prostate gland, secreting other components of seminal fluid
cell of bulbourethral gland, secreting mucus
cell of Bartholin's gland, secreting vaginal lubricant
cell of gland of Littre, secreting mucus
cell of endometrium of uterus, secreting mainly carbohydrates
isolated goblet cell of respiratory and digestive tracts, secreting mucus
mucous cell of lining of stomach
zymogenic cell of gastric gland, secreting pepsinogen
oxyntic cell of gastric gland, secreting HCl
acinar cell of pancreas, secreting digestive enzymes and bicarbonate
Paneth cell of small intestine, secreting lysozyme
type II pneumocyte of lung, secreting surfactant
Clara cell of lung
Cells Specialized for Secretion of Hormones cells of anterior pituitary, secreting
   growth hormone
   follicle-stimulating hormone
   luteinizing hormone
   prolactin
   adrenocorticotropic hormone
   thyroid-stimulating hormone
cell of intermediate pituitary, secreting melanocyte-stimulating hormone
cells of posterior pituitary, secreting
   oxytocin
   vasopressin
cells of gut and respiratory tract, secreting
   serotonin
   endorphin
   somatostatin
   gastrin
   secretin
   cholecystokinin
   insulin
   glucagons
   bombesin

TABLE 1-continued

Examples of Target Cells cells of thyroid gland, secreting
   thyroid hormone
   calcitonin
cells of parathyroid gland, secreting
   parathyroid hormone
   oxyphil cell
cells of adrenal gland, secreting
   epinephrine
   norepinephrine
   steroid hormones
      mineralocorticoids
      glucocorticoids
cells of gonads, secreting
   testosterone
   estrogen
   progesterone
cells of juxtaglomerular apparatus of kidney
   juxtaglomerular cell
   macula densa cell
   peripolar cell
   mesangial cell
Epithelial Absorptive Cells in Gut, Exocrine Glands,
and Urogenital Tract brush border cell of intestine
striated duct cell of exocrine glands
gall bladder epithelial cell
brush border cell of proximal tubule of kidney
distal tubule cell of kidney
nonciliated cell of ductulus efferens
epididymal principal cell
epididymal basal cell
Cells Specialized for Metabolism and Storage hepatocyte
fat cells (e.g., adipocyte)
   white fat
   brown fat
   lipocyte of liver
Epithelial Cells Serving Primarily a Barrier Function,
Lining the Lung, Gut, Exocrine Glands, and
Urogenital Tract type I pneumocyte
pancreatic duct cell
nonstriated duct cell of sweat gland, salivary gland, mammary gland, etc.
parietal cell of kidney glomerulus
podocyte of kidney glomerulus
cell of thin segment of loop of Henle
collecting duct cell
duct cell of seminal vesicle, prostate gland, etc.
Epithelial Cells Lining Closed Internal Body Cavities vascular endothelial cells of blood vessels and lymphatics
(e.g., microvascular cell)
   fenestrated
   continuous
   splenic
synovial cell
serosal cell
squamous cell lining perilymphatic space of ear
cells lining endolymphatic space of ear
   squamous cell
   columnar cells of endolymphatic sac
      with microvilli
      without microvilli
   "dark" cell
   vestibular membrane cell
   stria vascularis basal cell
   stria vascularis marginal cell
   cell of Claudius
   cell of Boettcher
choroid plexus cell
squamous cell of pia-arachnoid
cells of ciliary epithelium of eye
   pigmented
   nonpigmented
corneal "endothelial" cell TABLE 1-continued Examples of Target Cells Ciliated Cells with Propulsive Function of respiratory tract
of oviduct and of endometrium of uterus
of rete testis and ductulus efferens
of central nervous system
Cells Specialized for Secretion of Extracellular Matrix epithelial:
   ameloblast
   planum semilunatum cell of vestibular apparatus of ear
   interdental cell of organ of Corti
nonepithelial:
   fibroblasts
   pericyte of blood capillary (Rouget cell)
   nucleus pulposus cell of intervertebral disc
   cementoblast/cementocyte
   odontoblast/odontocyte
   chondrocytes
     of hyaline cartilage
     of fibrocartilage
     of elastic cartilage
   osteoblast/osteocyte
   osteoprogenitor cell
   hyalocyte of vitreous body of eye
   stellate cell of perilymphatic space of ear
Contractile Cells skeletal muscle cells
   red
   white
   intermediate
   muscle spindle-nuclear bag
   muscle spindle-nuclear chain
   satellite cell
heart muscle cells
   ordinary
   nodal
   Purkinje fiber
   Cardiac valve tissue
smooth muscle cells
myoepithelial cells:
   of iris
   of exocrine glands
Cells of Blood and Immune System red blood cell (erythrocyte)
megakaryocyte
macrophages
   monocyte
   connective tissue macrophage
   Langerhan's cell
   osteoclast
   dendritic cell
   microglial cell
neutrophil
eosinophil
basophil
mast cell
plasma cell
T lymphocyte
   helper T cell
   suppressor T cell
   killer T cell
B lymphocyte
   IgM
   IgG
   IgA
   IgE
killer cell
stem cells and committed progenitors for the blood and immune system
Sensory Transducers photoreceptors
   rod
   cones
     blue sensitive
     green sensitive
     red sensitive
hearing
   inner hair cell of organ of Corti
   outer hair cell of organ of Corti
acceleration and gravity
   type I hair cell of vestibular apparatus of ear
   type II hair cell of vestibular apparatus of ear
taste
   type II taste bud cell
smell
   olfactory neuron
   basal cell of olfactory epithelium
blood pH
   carotid body cell
     type I
     type II
touch
   Merkel cell of epidermis
   primary sensory neurons specialized for touch
temperature
   primary sensory neurons specialized for temperature
     cold sensitive
     heat sensitive
pain
   primary sensory neurons specialized for pain
configurations and forces in musculoskeletal system
   proprioceptive primary sensory neurons
Autonomic Neurons cholinergic
adrenergic
peptidergic
Supporting Cells of Sense Organs and of Peripheral Neurons supporting cells of organ of Corti
   inner pillar cell
   outer pillar cell
   inner phalangeal cell
   outer phalangeal cell
   border cell
   Hensen cell
supporting cell of vestibular apparatus
supporting cell of taste bud
supporting cell of olfactory epithelium
Schwann cell
satellite cell
enteric glial cell
Neurons and Glial Cells of Central Nervous System neurons
glial cells
   astrocyte
   oligodendrocyte
Lens Cells anterior lens epithelial cell
lens fiber
Pigment Cells melanocyte
retinal pigmented epithelial cell
iris pigment epithelial cell
Germ Cells oogonium/oocyte
spermatocyte
Spermatogonium
blast cells
fertilized ovum
Nurse Cells ovarian follicle cell
Sertoli cell
thymus epithelial cell (e.g., reticular cell)
placental cell Introducing Exogenous Nucleic Acids into Host Cells.

Cells of the invention include one or more nucleic acid constructs encoding a gene switch/biosensor and a gene amplification system. Use of such constructs to stably introduce exogenous nucleic acids into cells is generally known in the art and is described in methodology references such as Gene Therapy Methods: ed. M. I. Phillips, Academic press, 2002; Viral Vectors, eds. Yakov Gluzman and Stephen H. Hughes, Cold Spring Harbor Laboratory Press, Cold Spring Harbor, N.Y., 1988; Retroviruses, Cold Spring Harbor Laboratory Press, Plainview, N.Y., 2000; Gene Therapy Protocols (Methods in Molecular Medicine), ed. Jeffrey R. Morgan, Humana Press, Totawa, N.J., 2001; and Molecular Cloning: A Laboratory Manual, 3nd ed., vol. 1-3, ed. Sambrook et al., Cold Spring Harbor Laboratory Press, Cold Spring Harbor, N.Y., 2001.

Viral vectors are presently preferred for introducing a gene switch/biosensor and gene amplification system into cells. Viral vector methods and protocols are reviewed in Kay et al. *Nature Medicine* 7:33-40, 2001. Preferred viral vectors for use in the invention are recombinant AAV (rAAV) vectors. rAAV-mediated gene transfer is safe, stable and long-lasting. AAV-based vectors exhibit a high transduction efficiency of target cells and can integrate into the host genome in a site-specific manner. Methods for use of rAAV vectors are discussed, for example, in Tal, J., J. Biomed. Sci. 7:279-291, 2000 and Monahan and Samulski, Gene Therapy 7:24-30, 2000. As shown in FIG. 1, a first preferred rAAV vector in a gene switch/biosensor and gene amplification system (the sensor vector) contains a pair of AAV (inverted terminal repeats) ITRs which flank at least one cassette containing a promoter (e.g., a CMV promoter) which directs expression of an operably linked nucleotide sequence encoding a chimeric transactivator (e.g., GAL4DBD/ODD/p65AD). The second preferred rAAV vector (effector vector) contains a pair of AAV ITRs which flank several copies of a GAL4 UAS linked to a TATA element and therapeutic or protective gene (e.g., HO-1 alpha). Techniques involving nucleic acids and viruses of different AAV serotypes are known in the art and are described in Halbert et al., *J. Virol.* 74:1524-1532, 2000; Halbert et al., *J. Virol.* 75:6615-6624, 2001; and Auricchio et al., *Hum. Molec. Genet.* 10:3075-3081, 2001. The rAAV vectors and rAAV virions used in the invention may be derived from any of several AAV serotypes including 1, 2, 3, 4, 5, 6, 7, and 8. Preferred rAAV vectors for use in the invention are derived from serotype 2. Particular AAV vectors and AAV proteins of different serotypes are discussed in Chao et al., *Mol. Ther.* 2:619-623, 2000; Davidson et al., *Proc. Nat'l. Acad. Sci. USA* 97:3428-3432, 2000; and Xiao et al., *J. Virol.* 72:2224-2232, 1998.

Other rAAV virions useful in the invention have mutations within the virion capsid. For example, rAAV mutants may have ligand insertion mutations for the facilitation of targeting rAAV virions to specific cell types (e.g., cardiac myocytes or pancreatic beta cells). The construction and characterization of rAAV capsid mutants including insertion mutants, alanine screening mutants, and epitope tag mutants is described in Wu et al., *J Virol.* 74:8635-45, 2000. Pseudotyped rAAV virions in which an rAAV vector derived from a particular serotype is encapsidated within a capsid containing proteins of another serotype may be used in methods of the invention (Halbert et al., *J. Virol.* 74:1524-1532, 2000; Auricchio et al., *Hum. Molec. Genet.* 10:3075-3081, 2001). Pseudotyped rAAV virions having mutations within the capsid may also be useful for introducing a gene switch/biosensor and gene amplification system to cells. Other rAAV virions that can be used in methods of the invention include those capsid hybrids that are generated by molecular breeding of viruses as well as by exon shuffling. See Soong et al., *Nat. Genet.* 25:436-439, 2000; and Kolman and Stemmer *Nat. Biotechnol.* 19:423-428, 2001.

In addition to AAV, other viruses may be used to create vectors useful in preparing the vigilant cells of the invention. A list of such viruses include adenovirus (Ad) (see, W. C. Russell, *Journal of General Virology* 81:2573-2604, 2000, and Bramson et al., Curr. Opin. *Biotechnol.* 6:590-595, 1995), Herpes Simplex Virus (see, Cotter and Robertson, *Curr. Opin. Mol. Ther.* 1:633-644, 1999), lentiviruses (see, Vigna and Naldini, *J. Gene Med.* 5:308-316, 2000 and Miyoshi et al., *J. Virol.* 72:8150-8157, 1998), retroviruses (see Hu and Pathak, *Pharmacol. Rev.* 52:493-511, 2000 and Fong et al., *Crit. Rev. Ther. Drug Carrier Syst.* 17:1-60, 2000), and others (e.g., alphaviruses such as Semliki Forest Virus and Sindbis Virus).

Several non-viral methods for introducing a gene switch/biosensor and gene amplification system into host cells might also be used. For a review of non-viral methods, see Nishikawa and Huang, *Human Gene Ther.* 12:861-870, 2001 and M. I. Phillips, Gene Therapy Methods, Academic press, 2002. Various techniques employing plasmid DNA for the introduction of transactivator (e.g., GAL4 DBD/ODD/p65AD) and reporter sequences (e.g., several copies of a GAL4 UAS linked to a TATA element and therapeutic gene (e.g., cardioprotective gene) into cells are provided for according to the invention. Such techniques are generally known in the art and are described in references such as Ilan, Y., *Curr. Opin. Mol. Ther.* 1:116-120, 1999, Wolff, J. A., *Neuromuscular Disord.* 7:314-318, 1997 and Arztl, Z., Fortbild Qualitatssich 92:681-683, 1998.

In addition to virus-based methods, techniques involving physical introduction of a gene switch/biosensor and gene amplification system into a host cell that might be used include the particle bombardment method (see Yang et al., *Mol. Med. Today* 2:476-481 1996 and Davidson et al., *Rev. Wound Repair Regen.* 6:452-459, 2000), electroporation (see, Preat, V., *Ann. Pharm. Fr.* 59:239-244 2001), and cationic lipid-based methods (see, Felgner et al., *Ann. N.Y Acad. Sci.* 772:126-139, 1995 and Lasic and Templeton, *Adv. Drug Delivery Rev.* 20:221-266, 1996.)

The presence of exogenous nucleic acid constructs in cells can be monitored by conventional methods. For example, colonies of cells derived from rAAV vector-transduced cells can be assessed by PCR, flow cytometry and immunochemistry. The functional capacity of rAAV vector-transduced cells can be examined by quantifying clonogeneic efficiency and proliferative capacity. Frey et al., *Blood* 91:2781-2792, 1998. Following implantation of the transduced cells into the host, therapeutic gene expression can be analyzed by immunocytochemistry and RT-PCR of tissue samples. Condorelli et al., *Proc. Nat'l. Acad. Sci. USA* 98:10733-10738, 2001. PCR techniques may be used to identify and locate implanted cells that carry a rAAV vector and/or therapeutic gene. See Hou et al., *Proc. Nat'l. Acad. Sci. USA* 96:7294-7299, 1999.

Gene Switch/Biosensor and Gene Amplification System for Various Disease States.

Cells incorporating the dual vector system described above can be adapted to a particular disease state by using an appropriate tissue-specific promoter, an appropriate stimulus-responsive element, and appropriate therapeutic genes for treating the particular disease state. For example, the cells of the invention can be used to treat diabetes type 1 in a patient. For treating diabetes type 1, cells having both 1) a sensor vector containing a glucose-sensitive element, for example, in addition to the GAL4 DBD and p65 AD sequences and 2) an effector vector containing a pre-pro-insulin gene(s), for example, linked to the UAS and E1b TATA elements, might be used. After delivery to a target tissue (e.g., a pancreas or liver), the sensor vector in the cells detects elevated glucose levels and in response expresses a chimeric transactivator protein. The transactivator protein then binds to the effector vector and activates amplified expression of the pre-pro-insulin gene(s). When glucose levels are decreased the system switches off.

In another example, cells containing a gene switch/biosensor and gene amplification system can be used to treat cancer. Cells having a sensor vector that detects tumor markers and expresses a transactivator protein that activates anti-growth or anti-angiogenesis genes in the effector vector may be administered to the site of a tumor. A further example of a disease state to be treated using cells having a gene switch/biosensor and gene amplification system is stroke. Cells harboring a sensor vector responsive to hypoxia can express a transactivator protein that activates expression of the tPA gene in the effector vector. Such cells can be delivered to the brain of a subject at risk for stroke. To treat inflammatory diseases such as arthritis, pulmonary fibrosis and atherosclerosis, cells containing a sensor vector responsive to any of a number of atheroslcerosis indicators of inflammation including cytokines, MCP-1, c-reactive protein or elevated trigylceride, oxidised LDL cholesterol, Lp(a), homocysteine, and fibrinogen levels, as well as decreased HDL levels and endothelial-derived nitric oxide production, can be constructed. A transactivator protein expressed in response to such an indicator activates expression of a therapeutic gene in the effector vector. Therapeutic genes for atherosclerosis include those that encode: 1) proteins with hypolipidemic activity, 2) proteins that act on the cholesteryl ester transfer protein and lipase systems, 3) cholesterol-removing proteins, 4) proteins with fibrinolytic activity, 5) proteins that provide low density lipoprotein receptor replacement, and/or 6) proteins that induce vascular protection and disobliteration of occlusions (Sirtori, C. R., *Pharmacol. Ther.* 67:433-47, 1995) 7) HO-1 and 8) LOX-1 antisense. Other disease states include anemia and renal diseases that involve reduced oxygen. In the case of anemia, the therapeutic gene would be erythropoietin.

Therapeutic products encoded by vectors of the subject invention may also be interfering RNA, which reduce expression of a target gene within a cell in vitro or in vivo. The target gene may be endogenous to the cell, or may be exogenous to the cell, such as a viral gene or parasite gene.

Therapeutic gene products that occur naturally in a subject being treated are preferred over synthetic molecules or drugs because, for example, treating the subject with a naturally occurring gene product more accurately mimics the physiological state and reduces the likelihood that an adverse effect will occur (e.g., development of a tumor).

Cardioprotective Genes.

In preferred embodiments, cells of the invention include vectors that encode cardioprotective genes for protecting cells from ischemia in response to hypoxia. Several cardioprotective genes are known, including HO-1. This protein degrades the pro-oxidant heme and generates carbon monoxide and antioxidant bilirubin, conferring myocardial protection from ischemia/reperfusion injury. Franz et al., *Circ. Res.* 73:629-638, 1993. Another example of a cardioprotective gene is superoxide dismutase, which protects heart tissue from super oxide radicals generated during ischemia-reperfusion. Chen et al., *Circulation* 94:II412-II417, 1996; and Woo et al., *Circulation* 98:II255-II260, 1998. Genes that provide a protective effect from other cardiac disease states, such as heart degeneration and failure, may also be used in vectors of the invention. An example of a gene that improves cardiac function is phospholanban (PLN). The PLN gene product regulates the strength of each heartbeat and is known to malfunction in heart failure. Zvaritch et al. *J. Biol. Chem.* 275: 14985-14991, 2000. Any suitable cardioprotective gene that provides a therapeutically effective level of protection may be used in the invention.

A number of antisense molecules that confer a cardioprotective effect are known, including antisense to angiotensin II type-1 receptor (Yang et al., Circulation 96:922-926, 1997; and Yang et al., *Circ. Res.* 83:552-559, 1998), antisense to adrenergic beta-1 receptor (Chen et al., *Pharmacol. Exp. Ther.* 294:722-727, 2000), and antisense to angiotensin-converting enzyme that has been shown to protect rat hearts from ischemia-reperfusion (Chen et al., *Pharmacol. Exp. Ther.* 294:722-727, 2000).

Delivery of Cells to a Target Tissue. Delivery of vigilant cells to a target tissue in an animal subject is provided for within the invention. Any suitable method might be used (e.g., directly to the site through epicardial puncture or endoventricular injection, intracoronary injection with angioplasty, pericardial injection, transdermal injection, or systemic infusion).

The cells described above are preferably administered to a mammal in an effective amount, that is, an amount capable of producing a desirable result in a treated subject (e.g., protecting tissue from ischemia-mediated damage in the subject). As is well known in the medical and veterinary arts, dosage for any one animal depends on many factors, including the subject's size, body surface area, age, the particular composition to be administered, time and route of administration, general health, and drugs being administered concurrently. It is expected that an appropriate dosage of vigilant cells for delivery to a human subject would be in the range of about $10^6$ to $10^{10}$ cells. However, varying doses within the scope of the present invention will depend on the physiologic condition, size and weight of the subject and are evident to those of ordinary skill in the art.

As used in this specification, including the appended claims, the singular "a", "an", and "the" include plural reference unless the contact dictates otherwise. Thus, for example, a reference to "a polynucleotide" includes more than one such polynucleotide. A reference to "a nucleic acid sequence" includes more than one such sequence. A reference to "a cell" includes more than one such cell.

The terms "comprising", "consisting of" and "consisting essentially of" are defined according to their standard meaning. The terms may be substituted for one another throughout the instant application in order to attach the specific meaning associated with each term.

The term "polypeptide" refers to any polymer comprising any number of amino acids, and is interchangeable with "protein", "gene product", and "peptide".

A nucleic acid molecule can be isolated from a natural source, or it can be produced using recombinant DNA technology (e.g., polymerase chain reaction (PCR) amplification, cloning) or chemical synthesis. Nucleic acid molecules can be generated or modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules, and combinations thereof.

Although the phrase "nucleic acid molecule" (or "nucleotide molecule") primarily refers to the physical nucleic acid molecule and the phrase "nucleic acid sequence" primarily refers to the sequence of nucleotides on the nucleic acid molecule, the two phrases can be used interchangeably. As used herein, a "coding" nucleic acid sequence refers to a nucleic acid sequence that encodes at least a portion of a polypeptide (e.g., a portion of an open reading frame), and can more particularly refer to a nucleic acid sequence encoding a polypeptide which, when operatively linked to a transcription control sequence (e.g., a promoter sequence), can express the polypeptide.

The term "operably-linked" or "operatively linked" is used herein to refer to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence.

As used herein, the term "isolated" means removal from its native environment, and can include removal from its immediate native environment.

As used herein, the term "differentiated" refers to those cells that maintain in culture all, or a substantial amount of, their specialized structure and function typical of the cell type in vivo. Partially differentiated cells maintain less than a substantial amount of their full complement of specialized structure and/or function.

Nucleic acid constructs comprising a gene switch/biosensor and a gene amplification system may be introduced into stem cells. As used herein, the term "stem cell" is an unspecialized cell that is capable of replicating or self renewal, and developing into specialized cells of a variety of cell types. The product of a stem cell undergoing division is at least one additional stem cell that has the same capabilities of the originating cell. For example, under appropriate conditions, a hematopoietic stem cell can produce a second generation stem cell and a neuron. Stem cells include embryonic stem cells (e.g., those stem cells originating from the inner cells mass of the blastocyst) and adult stem cells (which can be found throughout the more mature animal, including humans). As used herein, stem cells are intended to include those stem cells found in animals that have matured beyond the embryonic stage (e.g., fetus, infant, adolescent, juvenile, adult, etc.). The list of tissues reported to contain stem cells is growing and includes, for example, bone marrow, peripheral blood, brain, spinal cord, umbilical cord blood, amniotic fluid, placenta, dental pulp, blood vessels, skeletal muscle, epithelia of the skin and digestive system, cornea, retina, liver, and pancreas.

Nucleic acid constructs comprising a gene switch/biosensor and a gene amplification system may be introduced into progenitor cells. As used herein, the term "progenitor cell" (also known as a precursor cell) is unspecialized or has partial characteristics of a specialized cell that is capable of undergoing cell division and yielding two specialized cells. For example, a myeloid progenitor/precursor cell can undergo cell division to yield two specialized cells (a neutrophil and a red blood cell).

As used herein, the term "phenotype" refers to all the observable characteristics of a cell (or organism); its shape (morphology); interactions with other cells and the non-cellular environment (e.g., extracellular matrix); proteins that appear on the cell surface (surface markers); and the cell's behavior (e.g., secretion, contraction, synaptic transmission).

As used herein, the terms "administer", "apply", "treat", "transplant", "implant", "deliver", and grammatical variations thereof, are used interchangeably to provide vectors of the subject invention to target cells in vitro (e.g., ex vivo) or in vivo, or provide genetically modified cells of the subject invention to a subject.

As used herein, the term "co-administration" and variations thereof refers to the administration of two or more agents simultaneously (in one or more preparations), or consecutively. For example, one or more types of genetically modified cells of the invention can be co-administered with other agents.

EXAMPLES

The invention can be illustrated by the following examples in which bone marrow-derived stem cells that incorporate a dual viral vector system for expressing cardio-protective genes are administered to infarcted heart tissue to protect cells from ischemia-induced damage.

Materials and Methods for Example 1

Culture of Mouse Mesenchyamal Stem Cells (MSCs).

Four to six-week-old male BALB/c mice obtained from Harlan Company were killed by an overdose of pentobarbital injected intraperitoneally. The mice were immersed in 70% alcohol for 8 minutes, after which time the tibia and femoral bones were excised and collected. Bone marrow was obtained by flushing the shaft of femur and tibia using a 27 g needle attached to a 3 ml syringe with Dulbecco's modified Eagle's medium (DMEM) containing antibiotics (100 U/ml penicillin G, 100 ug/mg streptomycin). The marrow was disaggregated by gently aspirating several times using the same needle and syringe. The cells thus obtained were centrifuged for 5 minutes at 2000 rpm. The resulting cell pellet was resuspended and the cell concentration was adjusted to $5 \times 10^7$ nucleated cells per ml in complete medium (DMEM supplemented with 20% fetal bovine serum (FBS) and 100 U/ml penicillin G and 100 ug/mg streptomycin). The cells were then placed into a 75 $cm^2$ Corning flask and cultured in a humidified incubator at 37° C. with 5% $CO_2$.

MSC Isolation and Expansion.

In the cultures, the medium was replaced every 4 days, keeping the adherent cells and discarding nonadherent cells. Each primary culture was passaged to two new flasks when the MSCs grew to approximately 70% confluence. After a series of passages, homogeneous MSCs that were devoid of hematopoietic cells resulted. These were used for cell transfection.

Vector Construction.

As shown in FIG. 1, a double plasmid system was developed that includes a sensor plasmid (pGS-ODD) derived from pGS-CMV, which expresses a chimeric transcription factor consisting of the yeast GAL4 DBD (DBD amino acids 1-93) and the human p65 AD (AD amino acids 283-551) from NF-κB under the control of a CMV enhancer/promoter. An ODD (amino acids 394-603 within HIF-1α) was amplified by PCR from pCEP4/HIF-1α and fused in frame between the coding sequences of GAL4DBD and p65 AD to generate pGS-ODD. The second component of the system is an effector plasmid (pGene-hHO-1) that was generated by replacing the LacZ gene in pGene-LacZ (INVITROGEN, Carlsbad, Calif.) with HO-1α cDNA. In the construct the HO-1α insert was driven by six copies of a 17bp GAL4 UAS and an adenovirus E1b TATA box.

The expression cassette of pGS-ODD was cloned into an AAV vector between two ITRs to generate the prAAV-GS-ODD. In the same way, the expression cassette of pGene-hHO-1 (GAL4UAS, E1bTATA box, human HO-1α and 6×His) was cloned into an AAV backbone that contains green fluorescent protein (GFP) to generate pAAV-hHO-1. This rAAV vector plasmid and helper plasmid pDG were cotransfected into 293 cells by the calcium phosphate precipitation method. Plasmid pDG carries the rAAV rep and cap genes, as well as Ad helper genes required for rAAV replication and packaging. The $CaPO_4$/DNA precipitate was incubated in the media at 37° C. and 5% $CO_2$ for about 48 hrs. After harvesting the cells, the produced virions were isolated by (1) placing the cells in lysis buffer, (2) performing three cycles of freezing and thawing the cells for three times and (3) low speed centrifugation to remove cellular debris. The rAAV in the resulting supernatant was further purified using a non-ionic iodixanol gradient separation followed by heparin affinity chromatography. The method results in more than 50% recovery of rAAV from a crude lysate and routinely produces virus that is more than 99% pure with particle-infectivity ratios of less than 100. The titering of rAAV stock was performed by quantitative competitive PCR (QC-PCR) and fluorescent cell assay.

Genetic Modification.

At a confluence of 50%~60%, MSCs were treated with 0.25% trypsin and 1 mM EDTA (Gibco, Carlsbad, Calif.) and replated. The next day, cells were infected with two viruses (AAV-MLC-ODD & AAV-hHO-1-6×His) using LipofectAMINE (INVITROGEN, Carlsbad, Calif.) according to manufacturer's protocol. Three days after the transduction, MSCs were put into hypoxia chambers (Oxygen Sensers) with 1% $O_2$, 5% $CO_2$, and 94% $N_2$, and then incubated at 37° C. After 5 hours, the cells were screened for GFP expression using an inverted microscope with appropriate filters. The GFP-positive clones were recognized and cloned to establish stable cell lines that express the reporter gene under hypoxia constitutively.

Cloning of Vigilant Cell.

Medium in the culture dish was removed and the dish was washed twice with phosphate-buffered saline (PBS) to remove any trace of serum. A cloning ring was placed over a selected green colony under a fluorescence microscope after hypoxia treatment. 75 µl of 0.25% trypsin 1 mM EDTA solution (GIBCO, Carlsbad, Calif.) was added to the center of the ring with a pipette. The dish was returned to the incubator for 15 min, after which time the colony was examined under a microscope to ensure the cells rounded up and detached. The area in the ring was pipetted to detach all cells, which were then transferred to centrifuge tube. Serum-containing medium was added to neutralize the trypsin. The cells were centrifuged and resuspended in culture medium and placed in culture. This procedure was repeated until stable hypoxia-responding MSCs clones were obtained. These were named "vigilant cells."

Vigilant Cell Expansion and Labeling.

Purified vigilant cells were further expanded in culture until the day of implantation. Prior to implantation, MSCs were stained with the fluorescent DNA-intercalating dye 4,6-diamidino-2-phenylindole (DAPI). Prior to injection the cells were thoroughly washed and kept at 4° C.

Myocardial Infarction (MI).

Mice (6 to 8-week-old male BALB/c) were anesthetized with sodium pentobarbital (40 mg/kg, i.p.) and then intubated with a 24-gauge intravenous catheter with a tapered tip via the oral cavity without tracheotomy. Mice were mechanically ventilated on a Harvard rodent ventilator Harvard Apparatus Co. Inc, Boston, Mass.) with room air (respiratory rate 110/min, tide volume: 0.3 ml, ventilatory rate of 110/min was found to produce optimal values of $PO_2$, $pCO_2$, and pH). Under the dissecting microscope, the chest was opened through a left thoracotomy in the fourth intercostal space using a microcoagulator. The medial aspect of the incision was extended cranically to form a flap that was retracted to expose the heart. A small opening was made in the pericardium and an 8-0 nylon suture was passed under the left anterior descending coronary artery 2-3 mm from the tip of the left auricle. Coronary occlusion was induced by ligating the suture. Successful performance of coronary occlusion was verified by visual inspection (noting the development of a pale color in the distal myocardium after ligation). After the coronary occlusion protocol was completed, the chest was closed in layers by a 5-0 polyester fiber suture with one layer through the chest wall. The muscle was closed with a polypropylene suture and the skin was closed with a stainless steel wound clip (removed 10 days post-operation). The animal subjects were removed from the respirator and kept warm by a heated water blanket and allowed 100% oxygen via nasal cone.

Vigilant Cell Implantation.

One week after MI induction, 10 mice were injected with DAPI-labeled vigilant cells ($6 \times 10^6$ in 50 µl of DMEM medium), and 10 mice were injected with DAPI-labeled MSCs as follows. Anesthesia was induced and maintained. Mice were intubated and ventilated. The heart was re-exposed via formal left thoracotomy incision. Under direct vision, the cell suspension was injected into the peri-infarct region with a 31-gauge needle. The chest was closed in layers and the mice were sacrificed at 7 days after cell therapy.

Immunohistochemistry on Heart Tissue.

The survival of implanted MSCs was examined in mice by measuring the DAPI positive cells in sections harvested from ischemic myocardium as follows. Mice in both groups were sacrificed at 1 week after cell implantation. Heart sections harvested from the left ventricle were embedded in Tissue-Tek O.C.T. compound (Miles Inc, Elkhart, Ind.), then snap-frozen in dry ice. DAPI-positive MSC nuclei were quantified in frozen sections by fluorescence microscopy (Zeiss Axioplan 2 microscope). The survival of vigilant cells was compared to that of control MSCs. Heart sections were selected by immunofluorescent staining for hHO-1 as follows. Sections were incubated in primary antibodies, the mouse anti-human heme oxygenase 1 $IgG_1$ (BD Transduction Laboratories, San Jose, Calif.), at a 1:50 dilution for 30 minutes at 37° C., and then incubated with secondary antibodies, goat anti-mouse IgG-TRITC conjugate (SIGMA, Saint Louis, Mo.), at a 1:200 dilution for 30 minutes in 37° C.

Regeneration of Myocardial Tissue.

The following cardiac markers were tested using primary mouse monoclonal antibodies to the following: α-actin (sarcomeric) clone EA-53 (SIGMA, Saint Louis, Mo.); connexin-43 (BD Transduction Laboratories, San Jose, Calif.) and desmin (BD Transduction Laboratories). Sections were incubated in the respective primary antibodies at a 1:50 dilution for 30 minutes at 37° C., and then incubated in second antibody, goat anti-mouse IgG-TRITC conjugate (SIGMA, Saint Louis, Mich.), at a 1:200 dilution for 30 minutes in 37° C. Combined DAPI and TRITC images were made by using a simultaneous excitation filter under fluorescence microscopy (Zeiss Axioplan 2 microscope). Digital images were transferred to a computer equipped with Spot Software (Diagnostic Instruments, Inc., Sterling Heights, Mich.) for analysis.

Apoptosis.

Five μm cryosections cut from the midcavity of mouse heart were stained with fluorescent TUNEL using a commercially available kit (TUNEL Apoptosis Detection Kit upstate, Lake Placid, N.Y.) according to the manufacturer's instructions. In brief, thin myocardial sections were treated with proteinase K (250 μl); incubated with biotin-dUTP, TdT; and then treated with avidin-FITC. Apoptotic cells were visualized and acquired using a BIO-RAD 1024 ES Confocal Microscope. The number of TUNEL-positive cells was scored in peri-infarct regions. For each heart, the number of TUNEL-positive myocyte nuclei was scored per unit field. Images were taken at high magnification using 100×.

Example 1

Results

Figure 2A:
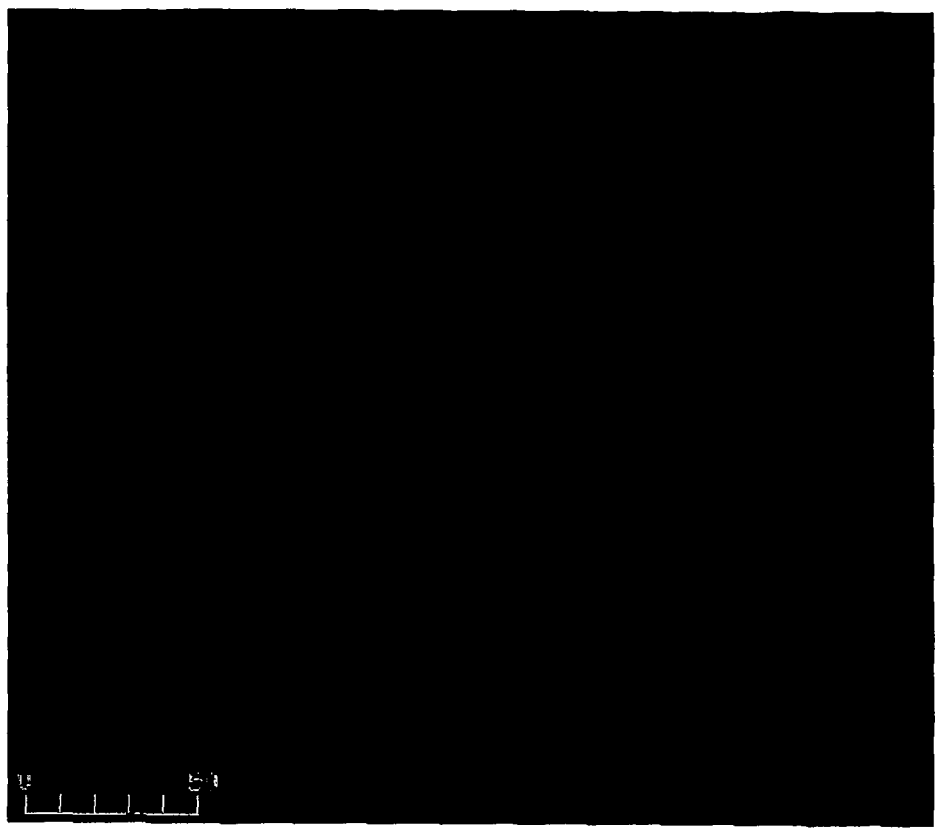
FIGS. 2A-2C are photomicrographs showing in vitro human heme oxygenase-1α (hHO-1) expression in vigilant cells under hypoxic (FIG. 2A) versus normoxic (normal oxygen) conditions (FIG. 2B), and a Western blot showing that total hHo-1 levels in hypoxia-treated MSCVHO-1 was on average 5.18-fold more abundant than at normoxia ($p<0.01$).
Figure 2B:
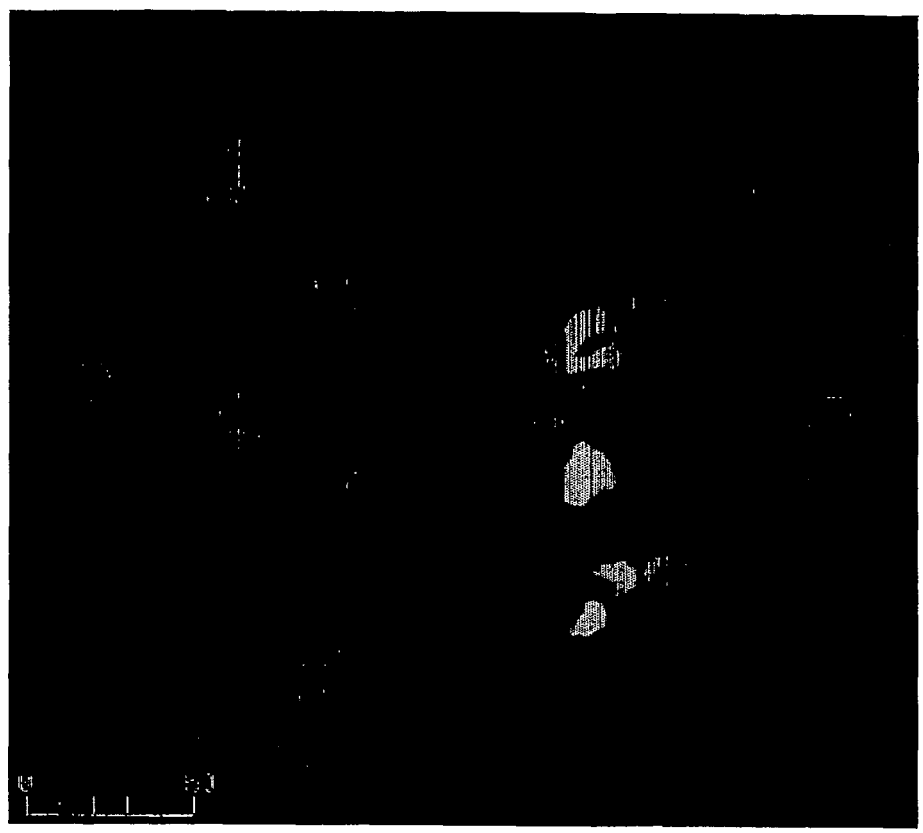

In vitro hHO-1 expression in vigilant cells under hypoxic conditions (FIG. 2A, with 1% $O_2$) was compared to the same cells under normoxic conditions (FIG. 2B, 20% $O_2$). MSCs were transfected with pGS-ODD and pGene-hHO-1 plasmids. The immunofluorescence staining with an antibody to hHO-1 revealed intense expression in the cells placed in hypoxic conditions. (×100, BIO-RAD Confocal microscope, Hercules, Calif.), but not in the cells placed in normoxic conditions.

Human HO-1 expression by vigilant cells in ischemic myocardium was examined after cell transplantation. Immunofluorescence staining for hHO-1 revealed expression of hHO-1 in grafted vigilant cells in the peri-infarct zone. Surviving vigilant cells were identified by DAPI-labeled nuclei as shown in FIG. 3B. Expression of hHO-1 (TRITC immunofluorescence) is shown in FIG. 3C. FIG. 3A shows both DAPI and TRITC staining. Most of the surviving vigilant cells stained with DAPI. Many of the cells in the transplant stained positively for hHO-1.

Figures 5A, 5B, 5C:
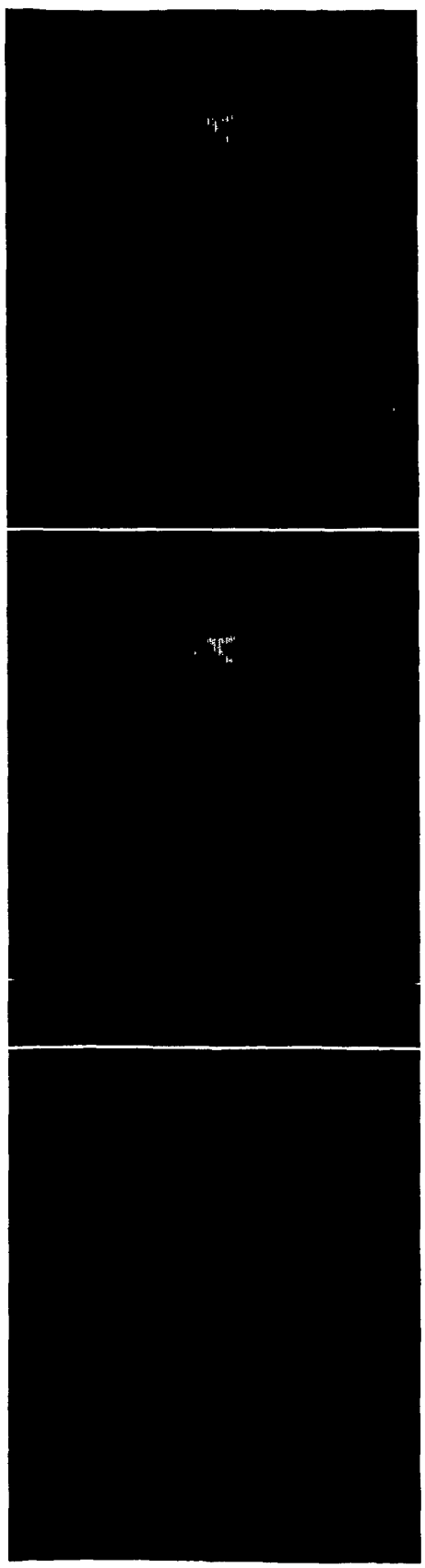
FIGS. 5A-5C are photomicrographs showing vigilant cells expressing Connexin43 in ischemic myocardium after cell transplantation. Surviving vigilant cells were identified by DAPI-labeled nuclei (FIG. 5B), connexin43 expression (TRITC) (FIG. 5C), and both DAPI and TRITC staining (FIG. 5A). It was observed that groups of cells were positively stained for connexin43 at injection sites in the peri-infarct area at 14 days after the transplantation of $MSC_{vHO-1}$, suggesting that some of the surviving MSCs had differentiated into myocyte-like cells within the native myocardium.

Connexin43 expression by vigilant cells in ischemic myocardium was examined after cell transplantation. Immunofluorescence staining for Connexin43 revealed that grafted Connexin43-expressing vigilant cells localized mainly in sites parallel to host myocardium. Surviving vigilant cells were identified by DAPI labeled nuclei as shown in FIG. 5B. Expression of Connexin43 (TRITC immunofluorscence) is shown in FIG. 5C. FIG. 5A shows both DAPI and TRITC staining. A portion of the vigilant cells in the transplant stained positively for Connexin43, an intercalated disk structure protein.

Figures 4A, 4B, 4C:
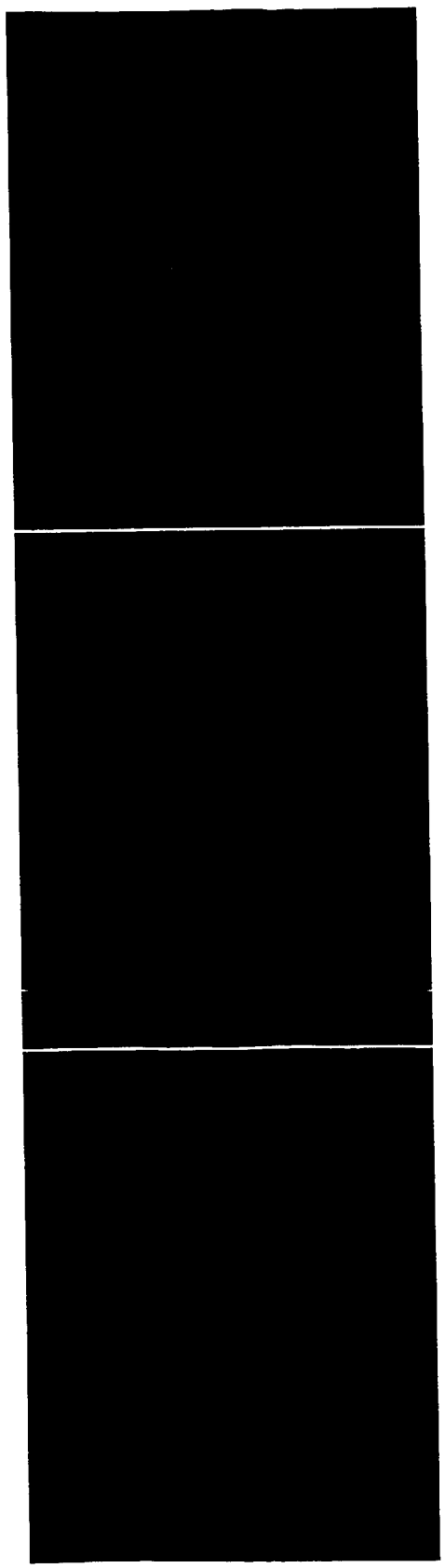
FIGS. 4A-4C are photomicrographs showing vigilant cells expressing α-actin in ischemic myocardium after cell transplantation. Surviving vigilant cells were identified by DAPI-labeled nuclei (FIG. 4B), α-actin expression (TRITC) (FIG. 4C), and both DAPI and TRITC staining (FIG. 4A). It was observed that groups of cells were positively stained for α-actin at injection sites in the peri-infarct area at 14 days after the transplantation of $MSC_{vHO-1}$, suggesting that some of the surviving MSCs had differentiated into myocyte-like cells within the native myocardium.

As shown in FIGS. 4A-4C, α-actin expression by vigilant cells in ischemic myocardium was examined after cell transplantation. Immunofluorescence staining for α-actin revealed expression of α-actin in grafted vigilant cells in the peri-infarct zone. Surviving vigilant cells were identified by DAPI-labeled nuclei as shown in FIG. 4B. Expression of α-actin (TRITC immunofluorscence) is shown in FIG. 4C. FIG. 4A shows both DAPI and TRITC staining. A portion of the vigilant cells in the transplant also stained positively for α-actin.

Figure 6A:
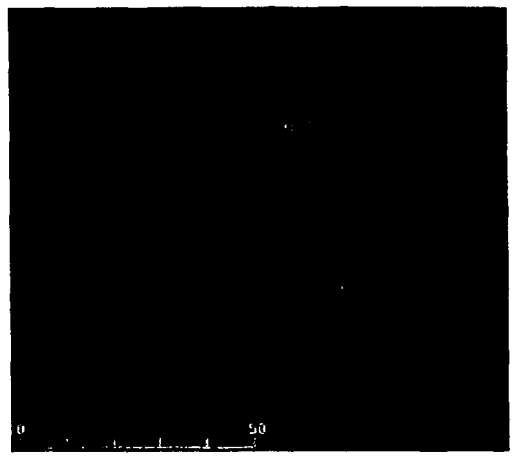
FIGS. 6A-6B are confocal images comparing apoptosis (TUNEL assay) in a vigilant cells group versus a mesenchymal stem cells (MSCs) group in the peri-infarct zone of ischemic myocardium 1 week after transplantation. Vigilant cell group (FIG. 6A); MSCs group (FIG. 6B).
Figure 6B:
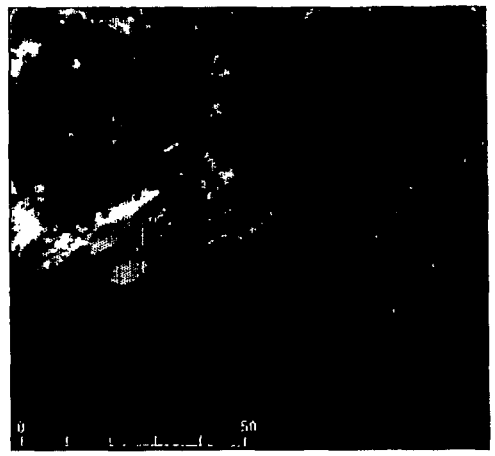

As shown in FIGS. 6A and 6B, apoptosis in the vigilant cells group versus MSCs in ischemic myocardium 1 week after transplantation was examined by TUNEL assay. Fewer apoptotic nuclei were observed in the vigilant cell group (FIG. 6A) than in the MSCs group (FIG. 6B) in the peri-infarct zone.

Materials and Methods for Examples 2-5

Animals.

All studies were performed with the approval of the institutional ethics committee. The investigation conformed to the Principles of Laboratory Animal Care formulated by the National Society for Medical Research and the Guide for the Care and Use of Laboratory Animals published by the US National Institutes of Health. Both donors and recipients were male BALB/c inbred mice weighing 20 to 25 g.

Cell Isolation, Culture, and Labeling.

Bone marrow was flushed from tibias and femurs using a 25 g needle. Whole marrow cells were cultured at $1\times10^6/cm^2$ in MesenCult basal medium supplemented with mesenchymal stem cell stimulatory supplements (StemCell Technologies Inc. Vancouver, Canada). The nonadherent cells were removed by a medium change at 72 hours and very 4 days thereafter. The monolayer, referred to as MSCs, was expanded by two passages. Before implantation, MSCs were trypsinized, washed, and labeled with 4',6-diamidino-2'-phenylindole DAPI, SIGMA-Aldrich Co, St. Louis, Mo.), as previously described. After labeling, DAPI stains specifically 100% of the MSCs nuclei.

Gene Construction and Gene Transfection.

Figure 7:
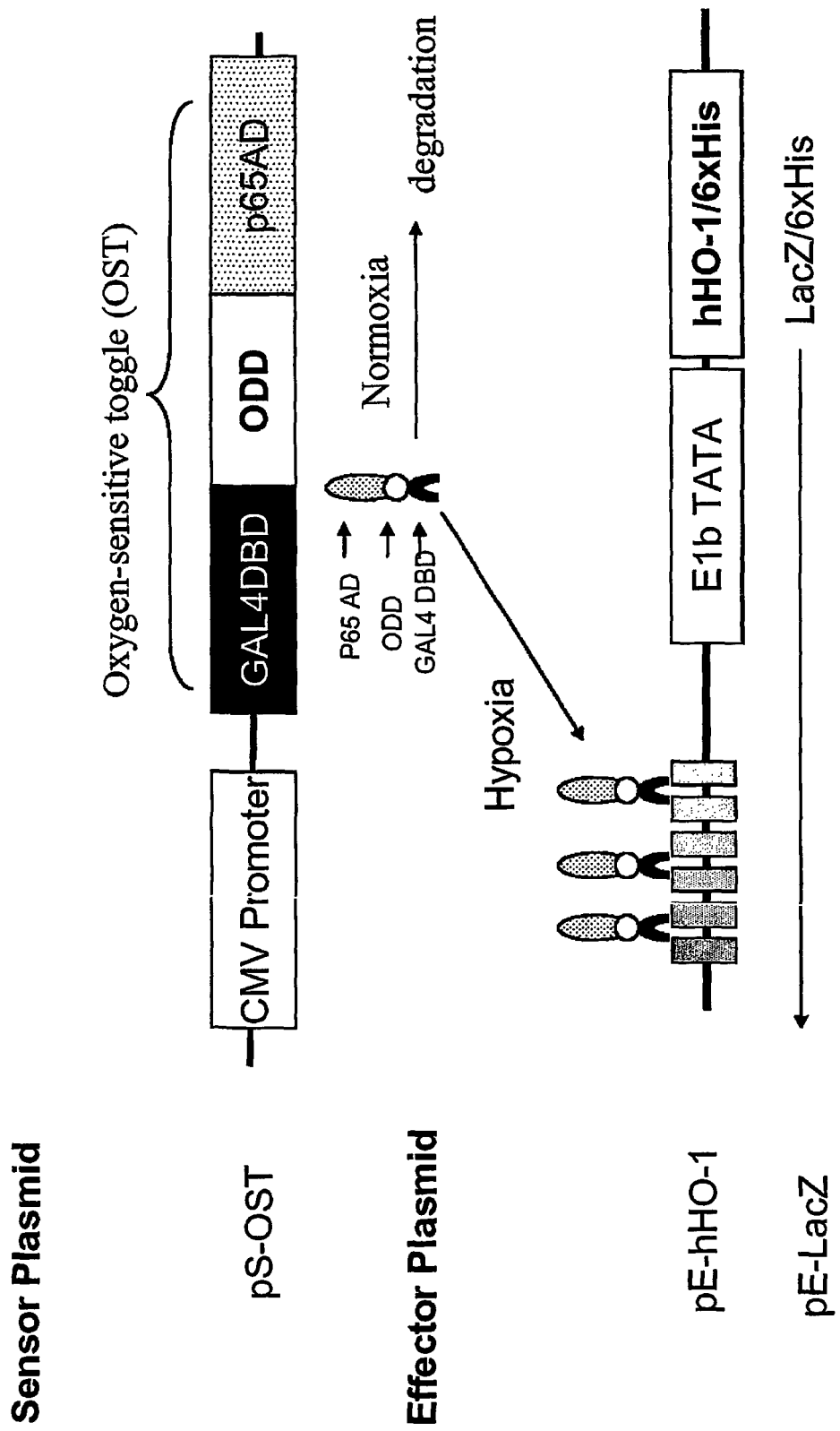
FIG. 7 shows a schematic diagram of two plasmid constructs used in the invention which contain vigilant hHO-1 system and vigilant LacZ system, including sensor plasmid (top) and effector plasmid (bottom).
Figure 8A:
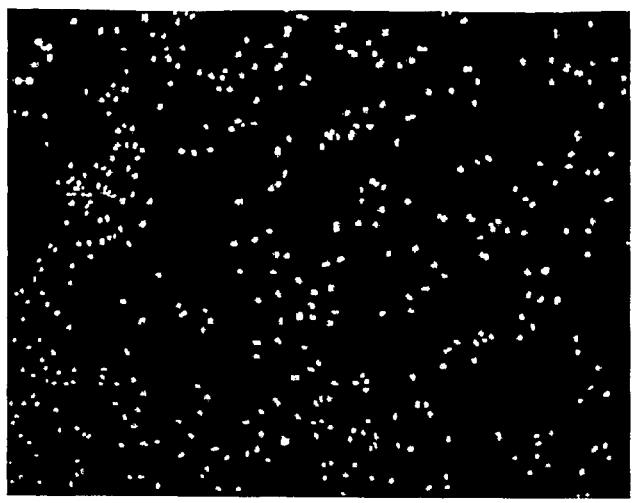
FIGS. 8A-8I are photomicrographs showing the effect of vigilant hHO-1 transfection on MSCs in vitro. To test the capability of $MSC_{VHO-1}$ to resist ischemia/reperfusion damage, the present inventors used hypoxic/normoxic/hypoxic treatment on $MSC_{vHO-1}$ with 24h hypoxia (1% $O_2$), 1 h normoxia (20% $O_2$) followed by another 24 h hypoxia. Most of $MSC_{VHO-1}$ expressed human HO-1 in immunocytostaining while negligible human HO-1 expression was seen in $MSC_{VlacZ}$ or MSCs. The increase in human HO-1 expression in $MSC_{VHO-1}$ was accompanied by a decrease in the MSCs apoptosis. As a result, the rate of cell apoptosis by the TUNEL in $MSC_{VlacZ}$ or MSCs (5.06±0.95 and 5.32±1.03 positive nuclei per 500 cells respectively) exceed that of $MSC_{vHO-1}$ (3.00±0.3 TUNEL+ per 500 cells) by 1.7-fold ($p<0.01$ for both $MSC_{VlacZ}$ and MSCs).
Figure 8B:
Figure 8C:
Figure 8D:
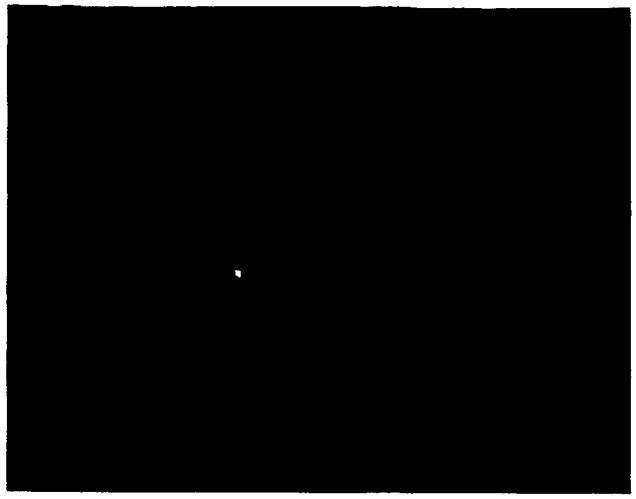
Figure 8E:
Figure 8F:
Figure 8G:
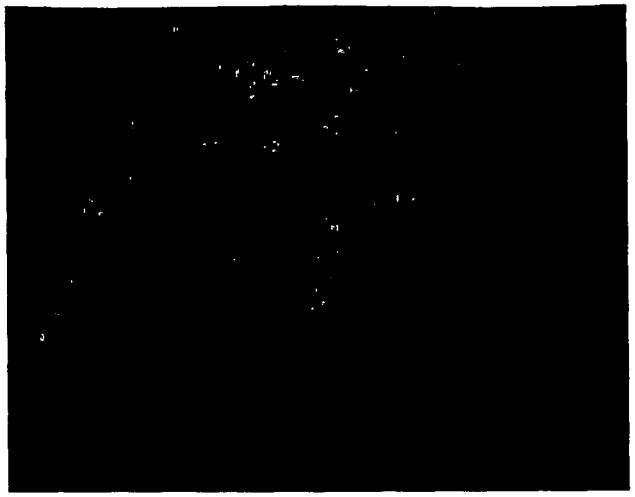
Figure 8H:
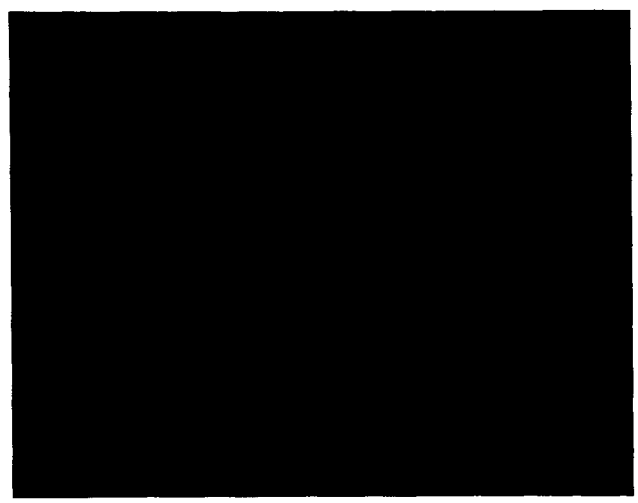
Figure 8I:

The vigilant plasmid system is a double-plasmid system, which contains a sensor plasmid with the oxygen sensitive toggle (OST) and effector plasmid with protective gene. In the sensor plasmid, (pS-CMV-OST), the oxygen-dependent degradation domain (ODD, amino acids 394-603) was amplified by PCR from pCEP4/HIF-1α and inserted in the frame between the coding sequence of GAL4 DNA binding domain and p65 activation domain in pS-CMV to generate pS-CMV-OST (FIG. 7). The effector plasmid (pEhHO-1) (FIG. 7) was constructed by replacing the LacZ coding sequence with full-length cDNA for human heme oxygenase-1α in pE/V5-His/LacZ (INVITROGEN Corporation, Calif.). A six-copy His tag was added to the C-terminal of hHO-1. Human HO-1 is driven by six copies of a 17-bp GAL4 UAS and an adenovirus-derived E1b TATA box. The construction of the plasmids was confirmed by nucleotide sequence analysis.

Polyethylenimine-Transferinfection Kit (Tf PEI-Kit, Bender MedSystems, Vienna, Austria) was prepared as described previously. Briefly, 2 plasmids (1:1) was mixed with a Tf PEI to generate a Tf PEI/DNA complex suspension. MSCs at 70% confluence were incubated with the Tf PEI/DNA containing the sensor plasmid and effector plasmid for 4 hours at 37° C. Control cells were transfected with vigilant vector with LacZ as reporter using the same protocol.

In Vitro Hapoxia Treatment and Apopotosis Assessment.

To evaluate hypoxia regulation of vigilant hHO-1 vectors in vitro, cell transfection and hypoxic treatment was performed as performed as described previously. MSCs was transfected with 1 μg pS-CMV-OST and 0.5 μg pE-hHO-1. Twenty-four hours after transfection, the medium was changed and MSCs were incubated at 1% or 20% O2 for 24 hours before preparation of lysates. Each condition was run in triplicate.

To test the capability of resistance ischemia/reperfusion damage of $MSC_{VHO-1}$, the present inventors used hypoxic/normoxic/hypoxic treatment on $MSC_{VHO-1}$ with 24 h hypoxia (1% O2) 1 hour normoxia (20% $O_2$) followed by another 24 h hypoxia. Western blot analysis was performed using 10-15 μg of whole cell. The hHO-1/6×His was probed with monoclonal anti-6×His antibody (INVITROGEN, Carlsbad, Calif.) and monoclonal anti-hHO-1 antibody (BD Biosciences, Palo Alto, Calif.). The pro-apoptosis protein Bax was probe with monoclonal anti-Bax antibody (Upstate, N.J.). The internal control protein GAPDH antibody (Chemicon, Temecula, Calif.) was probed for cells. The antigen-antibody complexes were visualized by enhanced chemiluminescence (Amersham, Piscataway, N.J.). For immunocytochemical analysis, MSCs were seeded into glass bottom microwell dishes (MatTek Corp, Ashland, Mass.) at day 2 after gene transfection for hypoxic treatment. The next day, samples were fixed with ice-cold ethanol. Half samples were incubated in a 1:50 dilution of anti-human HO-1 antibody (Santa Cruz Biotechnology) at 37° C. for 30 min, followed by incubation in a 1:500 dilution of FITCconjugated secondary antibody (SIGMA). The other samples were undergone TUNEL assay. Nuclei were counterstained with 10 µg/mL DAPI.

Myocardial Infarction Model and Cell Implantation.

Male BALB/c mice were anesthetized with sodium pentobarbital (40 mg/kg, i.p.) and mechanically ventilated. After the heart was exposed through a lateral thoracotomy, a 8-0 polypropylene thread was passed around the left coronary artery and the artery was occluded. At day 3 after gene transfection, MSCs were harvested using trypsin and resuspended in serum-free DMEM just before grafting to the heart. $1 \times 10_6$ of vigilant hHO-1-transfected-MSCs ($MSC_{VHO-1}$ group), vigilant lacZ-transfected MSCs ($MSC_{VlacZ}$ group), MSCs (MSCs group) or medium (medium group) in 50 µl volume was injected into syngenetic adult BALB/c mouse hearts in the border zone surrounding the infarct 1 hour after induction of myocardial infarction (injections of $1 \times 10^6$ cells in 50 µL) with a 30 G needle. The surgical wounds were repaired, and the mice were returned to their cages to recover. Aseptic surgical techniques were used throughout.

hHO-1 Expression and Differentiation of Grafted Cells in Ischemia Myocardium.

At 14 days after cell transplantation, 6 hearts from each group were collected to assess the hHO-1 expression of grafted MSCs. The frozen left ventricular samples were cut into 6-µm sections and fixed with −20° C. methanol. The sections were incubated with 0.6% H2O2, and immersed in 0.1% Triton X-100. After blocking with 1% bovine serum albumin, the sections were incubated with a 1:40 dilution of anti-HO-1 antibody (BD), anti-α-actin. This was followed by incubation with a 1:100 dilution of TRITC secondary antibody (SIGMA).

Functional Assessment.

At 14 days after cell transplantation, mice from 3 groups (n=6 in each group) were anticoagulated by an intravenous injection of heparin. Mice were anesthetized by pentobarbital (40 mg per kg (body weight), intraperitoneally (i.p.)). Mikro-Tip pressure catheter transducers (Model SPR-671, Millar Instruments, Inc, Houston, Tex.) were cannulated into the LV chamber through right carotid artery. The left ventricular pressure was digitized using the commercially available data acquisition system (PowerLab/8sp, ADinstruments, Inc.). After steady state had been established, LV systolic pressure (LVSP), LV develop pressures (LVDP), and maximal rates of pressure rise and fall (±dP/dt) were recorded in the closed-chest preparation.

Infarct Size and Myocardial Apoptosis.

After perfusion, the left ventricle was sectioned into 5 segments parallel to the apex-base axis and frozen in an embedding medium. A 10-µm section was cut from each segment, fixed in 3.7% formaldehyde, and stained with Masson trichrome. Sections from all slices were projected onto a screen for computer-assisted planimetry. The ratio of scar length to left ventricular circumferences of the endocardium and epicardium was expressed as a percentage to define infarct size, Average thick of infarct wall was also detected by planimetry.

Statistical Analysis.

All values are expressed as mean±SEM. The differences in the data between 2 groups were determined with a Student's t test. Statistical comparison of the data was performed with one-way ANOVA followed by LSD post-hoc testing. P<0.05 was considered significant.

Example 2

Human HO-1 Expression Protects Against MSC Apoptosis in Vitro

Several groups have reported the use of bone marrow-derived mesenchymal stem cells (MSCs) for restoration of cardiac function. However, progress in cell therapy has been hampered by poor viability of implanted cells and the vulnerability of regenerated tissue to repeated bouts of ischemia. To assess the hypothesis that genetically modified MSCs can increase the survival rate of implanted MSCs and afford self-protection of regenerated cardiomyocytes, the present inventors transfected MSCs with a vigilant plasmid system that expresses human heme oxygenase (hHO-1 α) in response to hypoxia.

Figure 2C:
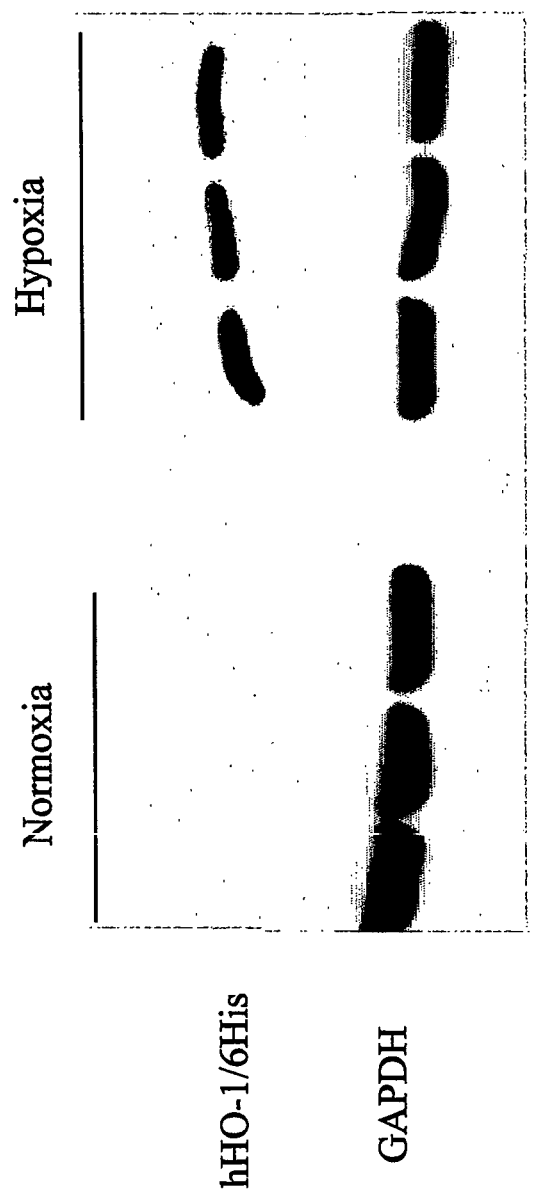

The MSCs isolated from the bone marrow of male BALb/C mice were grown to confluence and transfected with vigilant hHO-1, vigilant lacZ vector using polyethylenimine transfer-infection system. 80% of transfected MSCs were positively stained for human HO-1 after hypoxia treatment (1% $O_2$ for 24 hours). Immunocytostaining for human HO-1 demonstrated stronger hHO-1 expression in hypoxia treated $MSC_{VHO-1}$ compared to normoxia (FIGS. 2A and 2B). Western blot showed that total hHO-1 levels in hypoxia-treated MSCVHO-1 was on average 5.18-fold more abundant than at normoxia (P<0.01) (FIG. 2C). Because there is a fusion gene hHO-1/6His in the vector, the expressed fusion protein reacts only with antibody to human HO-1 or 6×his but not with endogenous mouse HO-1, these positively stained cells were presumed to be of vigilant hHO-1 origin in response to hypoxia, endogenous mouse HO-1 had no effect on the detection of vigilant HO-1 expression.

Figure 9:
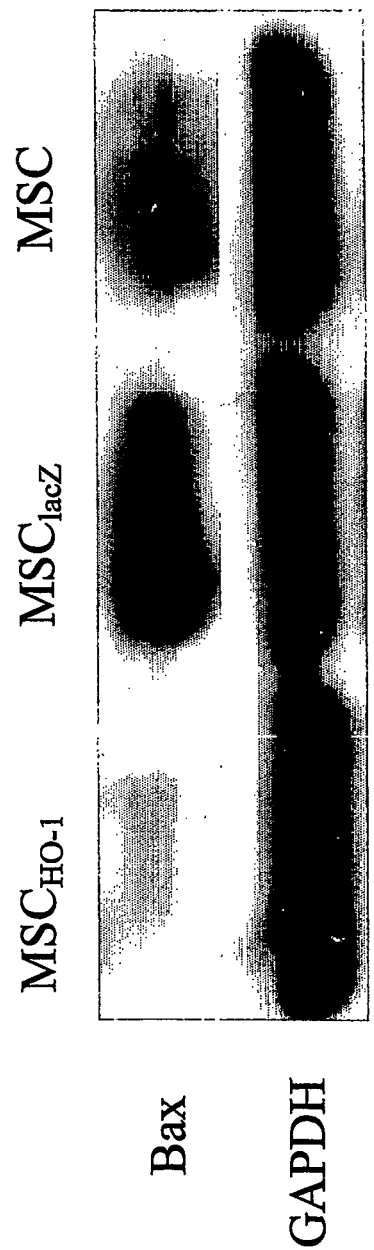
FIG. 9 shows a Western blot comparing expression level of the pro-apoptotic gene Bax in the cell lysate of $MSC_{VHO-1}$ in comparison with $MSC_{VlacZ}$ and MSCs.
Figure 10A:
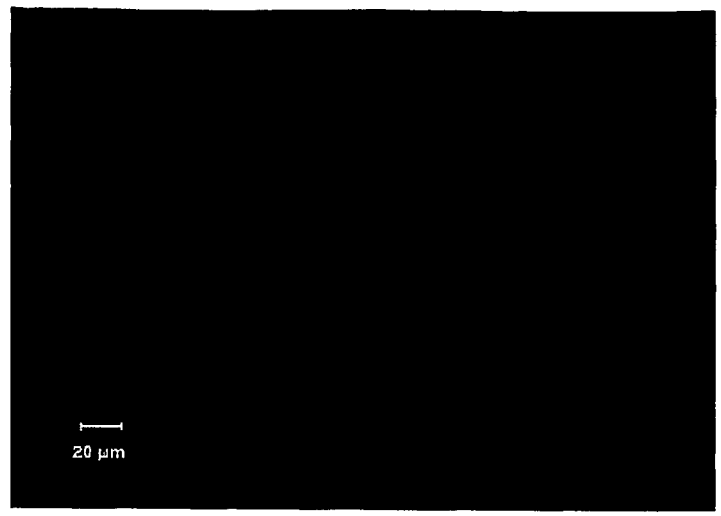
FIGS. 10A-10F show the effect of vigilant hHO-1 transfection on MSCs in ischemic myocardium. In the $MSC_{VHO-1}$ group, it was observed that a significantly smaller percentage of implanted cells were TUNEL positive (2.32±0.87 TUNEL+ per 200) (FIG. 10D) compared with the $MSC_{VlacZ}$ (4.98±0.90 TUNEL+ per 200, $p<0.01$ versus $MSC_{VHO-1}$) (FIG. 10E), and MSCs group (5.54±0.95 TUNEL+, $p<0.01$ versus $MSC_{VHO-1}$) (FIG. 10F).
Figure 10B:
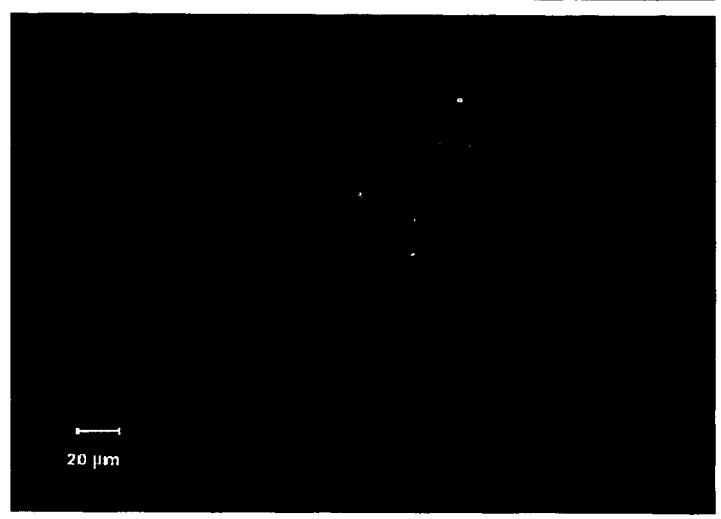
Figure 10C:
Figure 10D:
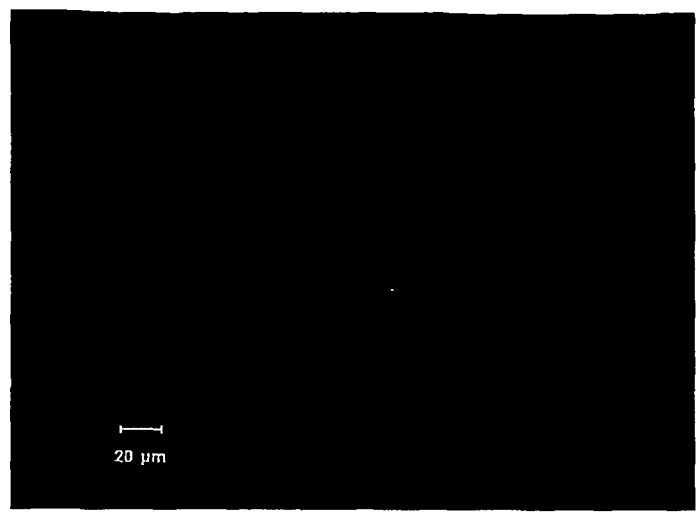
Figure 10E:
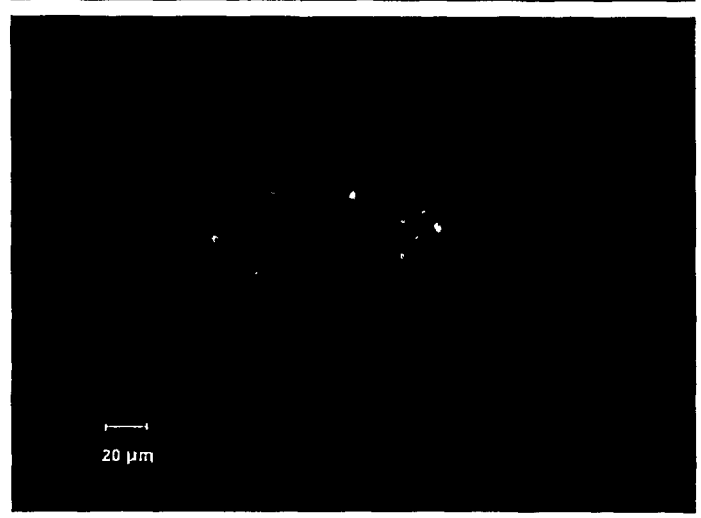
Figure 10F:
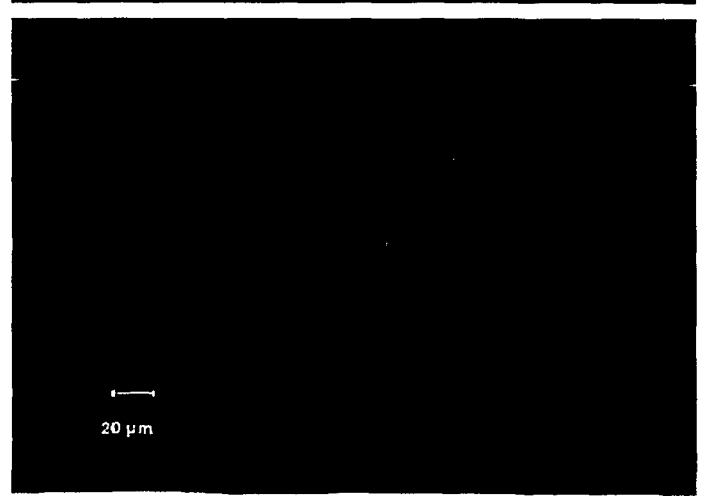
Figure 11A:
FIGS. 11A-11I are micrographs showing immunofluorescent staining of hHO-1 in ischemic myocardium, demonstrating a higher level of hHO-1 expression in most of the implanted cells in the $MSC_{VHO-1}$ group (FIG. 11D), compared with the $MSC_{VlacZ}$ (FIG. 11E) and MSCs group (FIG. 11F). Moreover, ischemic myocardium appeared to express higher hHO-1 level in the $MSC_{VHO-1}$ group than that of the medium group over the period studied.
Figure 11B:
Figure 11C:
Figure 11D:
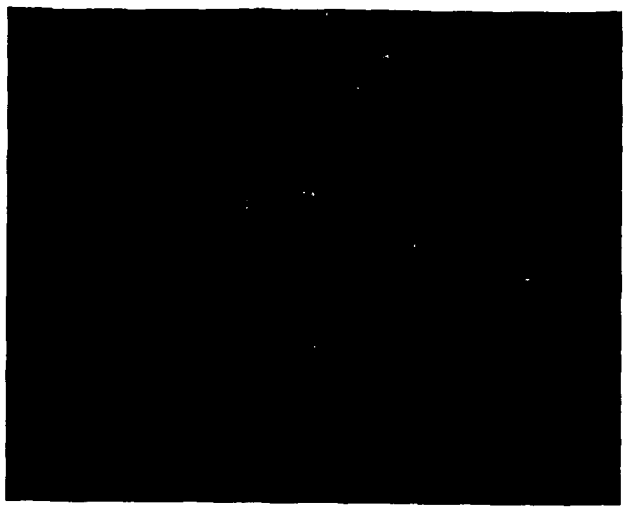
Figure 11E:
Figure 11F:
Figure 11G:
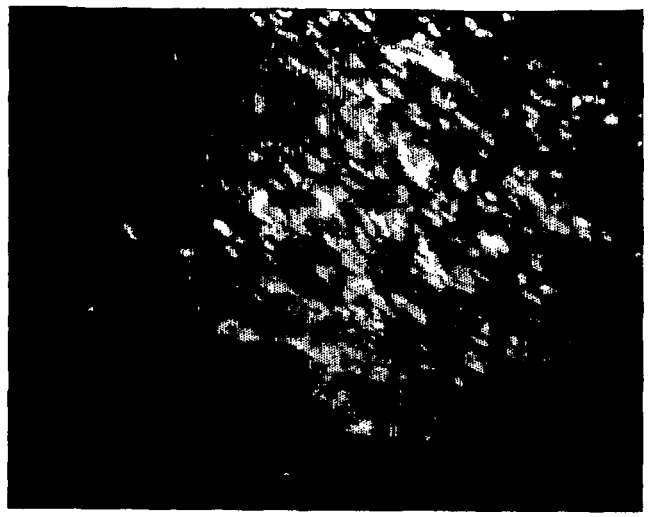
Figure 11H:
Figure 11I:
Figure 12B:
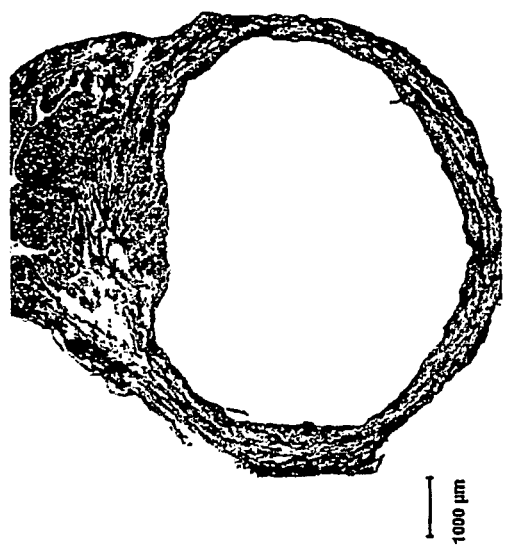
FIGS. 12A-12D show photomicrographs demonstrating injection of MSCs inhibits left ventricular remodeling. Hearts injected with MSCs post-myocardial infarction and stained with Masson showed infiltration of island-like extension of organized cardiac tissue into the myocardial scar.
Figure 12A:
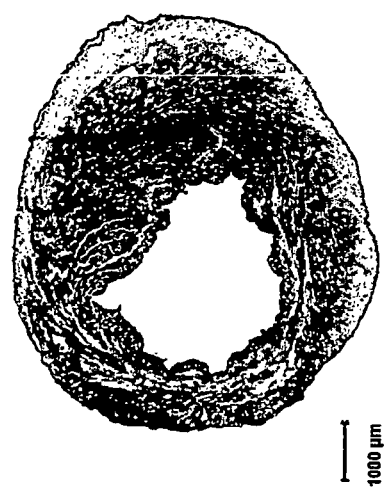
Figure 12D:
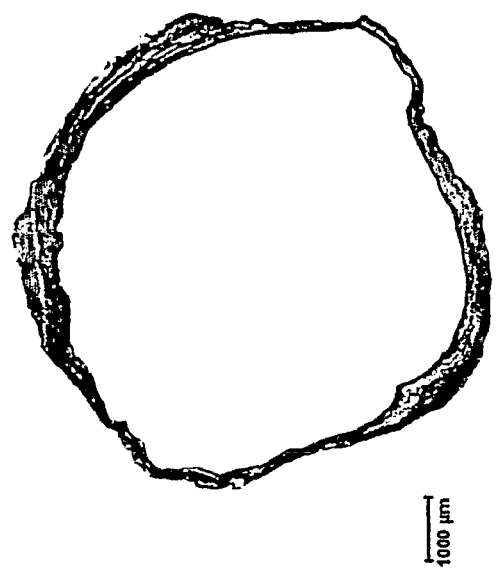
Figure 12C:
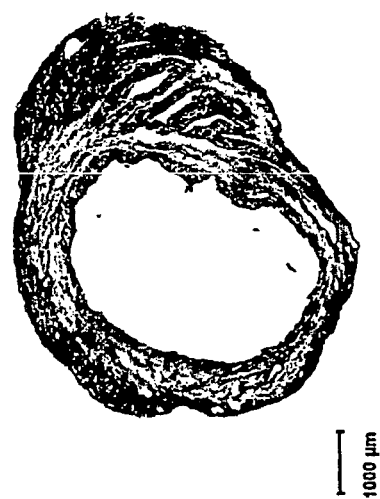
Figure 13A:
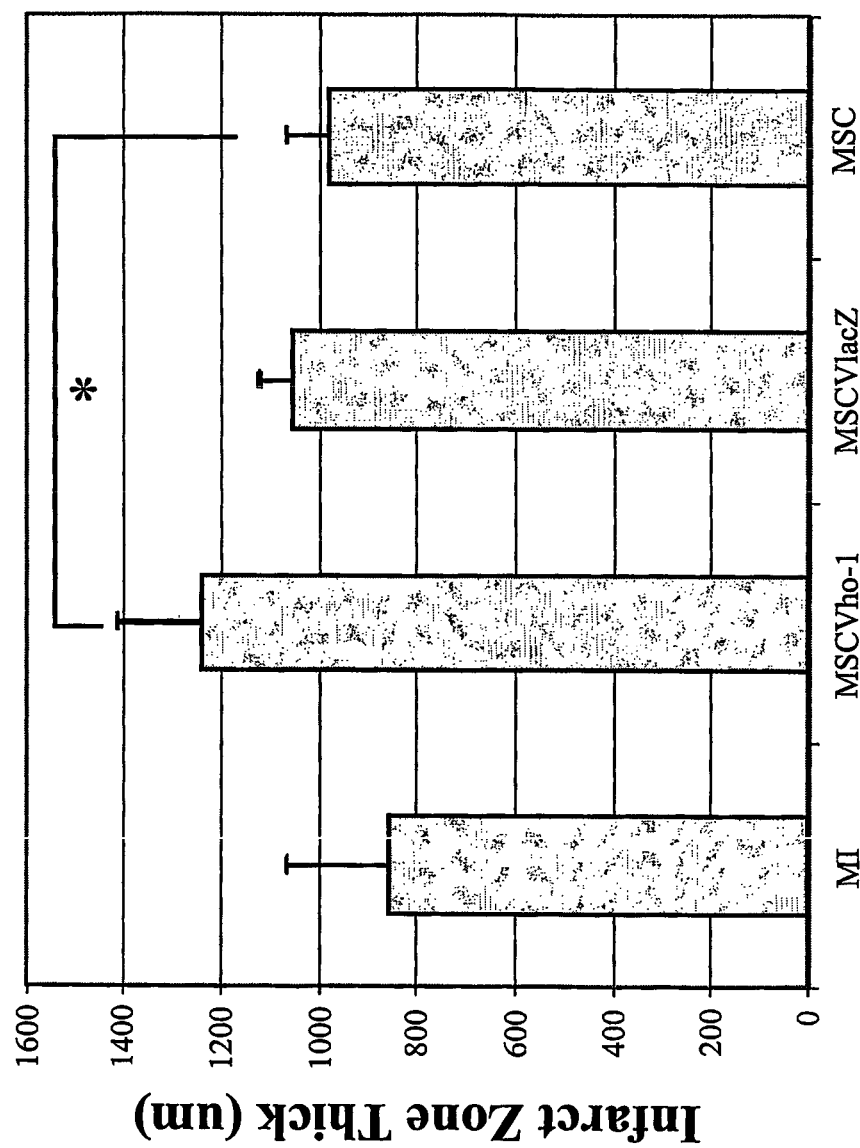
FIGS. 13A and 13B are bar graphs indicating that the $MSC_{vHO-1}$ group showed less infarct size than MSC groups in comparison with the medium group (38.9±18.8% versus 60.3±13.8%, $p=0.041$) (FIG. 13B); and the infarct wall of left ventricular was thicker in $MSC_{vHO-1}$ group in compared with MSC group (1239.9±174.1 μm versus 979.1±485.61 μm, $p=0.036$) (FIG. 13A).
Figure 13B:
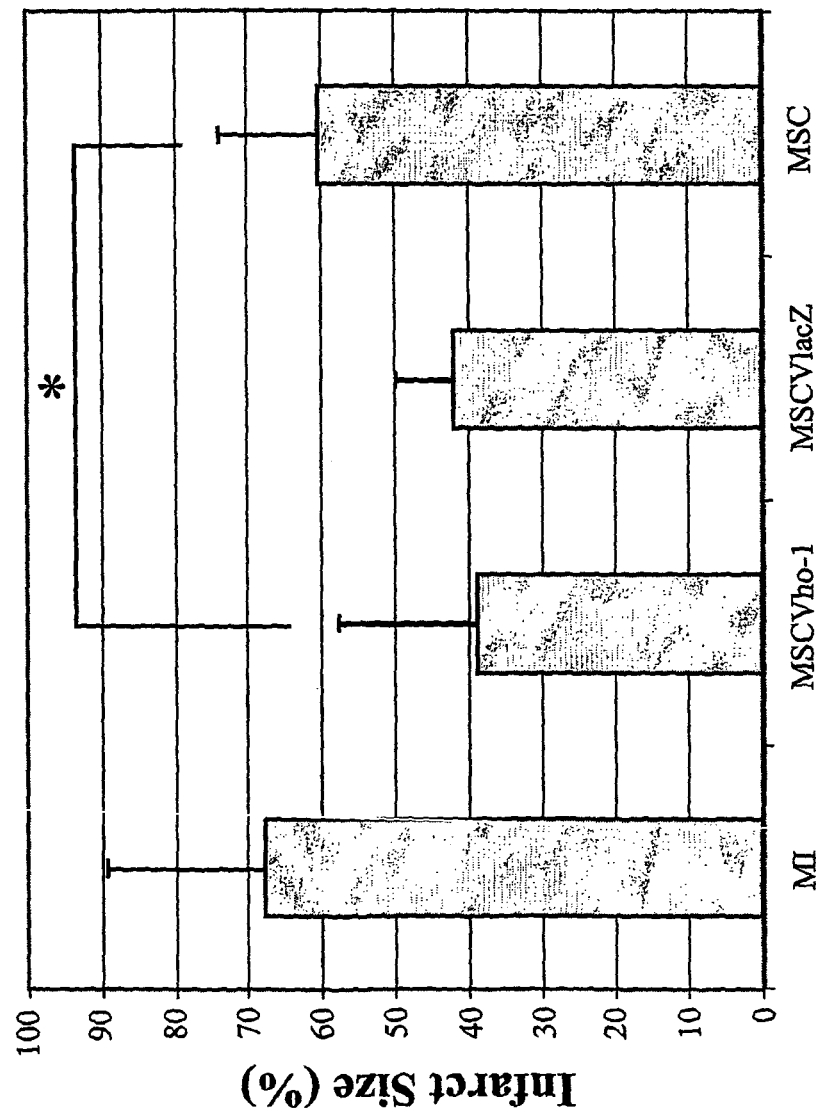

To test the capability of $MSC_{VHO-1}$ to resist ischemia/reperfusion damage, the present inventors used hypoxic/normoxic/hypoxic treatment on $MSC_{VHO-1}$ with 24 hour hypoxia (1% $O_2$), 1 hour normoxia (20% $O_2$) followed by another 24 h hypoxia. Most of $MSC_{VHO-1}$ expressed human HO-1 in immunocytostaining while negligible human HO-1 expression was seen in $MSC_{VlacZ}$ or MSCs (FIGS. 8A-8I). The increase in human HO-1 expression in $MSC_{VHO-1}$ was accompanied by a decrease in the MSCs apoptosis. As a result, the rate of cell apoptosis by the TUNEL in $MSC_{VlacZ}$ or MSCs (5.06±0.95 and 5.32±1.03 positive nuclei per 500 cells respectively) exceed that of $MSC_{VHO-1}$ (3.00±0.3 TUNEL+ per 500 cells) by 1.7-fold (p<0.01 for both $MSC_{VlacZ}$ and MSCs) (FIGS. 8A-8I). Similarly, a down-regulation in a pro-apoptotic gene Bax level in the cell lysate of $MSC_{VHO-1}$ was confirmed by Western blot in comparison with $MSC_{VlacZ}$ and MSCs (FIG. 9).

Example 3

Induction of Human HO-1 Expression in Ischemic Myocardium Protect against MSC Apoptosis in Vivo At 1 hour after myocardial infarction, the border zones of infarcts were injected with $1 \times 10^6$ $MSC_{VHO-1}$, $MSC_{VlacZ}$, MSCs or serum-free DMEM medium. At 12 days after injection, Apoptotic implanted cells were assessed in ischemic myocardium by TUNEL assay. In the MSCVHO-1 group, a significantly smaller percentage of implanted cells were TUNEL positive (2.32±0.87 TUNEL+ per 200) compared with the $MSC_{VlacZ}$ (4.98±0.90 TUNEL+ per 200, p<0.01 versus $MSC_{VHO-1}$) and MSCs group (5.54±0.95 TUNEL+, p<0.01 versus $MSC_{VHO-1}$) (FIG. 10A-10F). This finding is inversely correlated with immunofluorescent staining of hHO-1 in ischemic myocardium which demonstrated that higher level of hHO-1 expression in most of implanted cells in $MSC_{VHO-1}$ group, compared with the $MSC_{VlacZ}$ and MSCs group (FIGS. 11A-11I). Moreover, ischemic myocardium appeared to express higher hHO-1 level in the $MSC_{VHO-1}$ group than that of the medium group over the period studied.

Example 4

In Site Differentiation of Grafted MSCs

Figure 14:
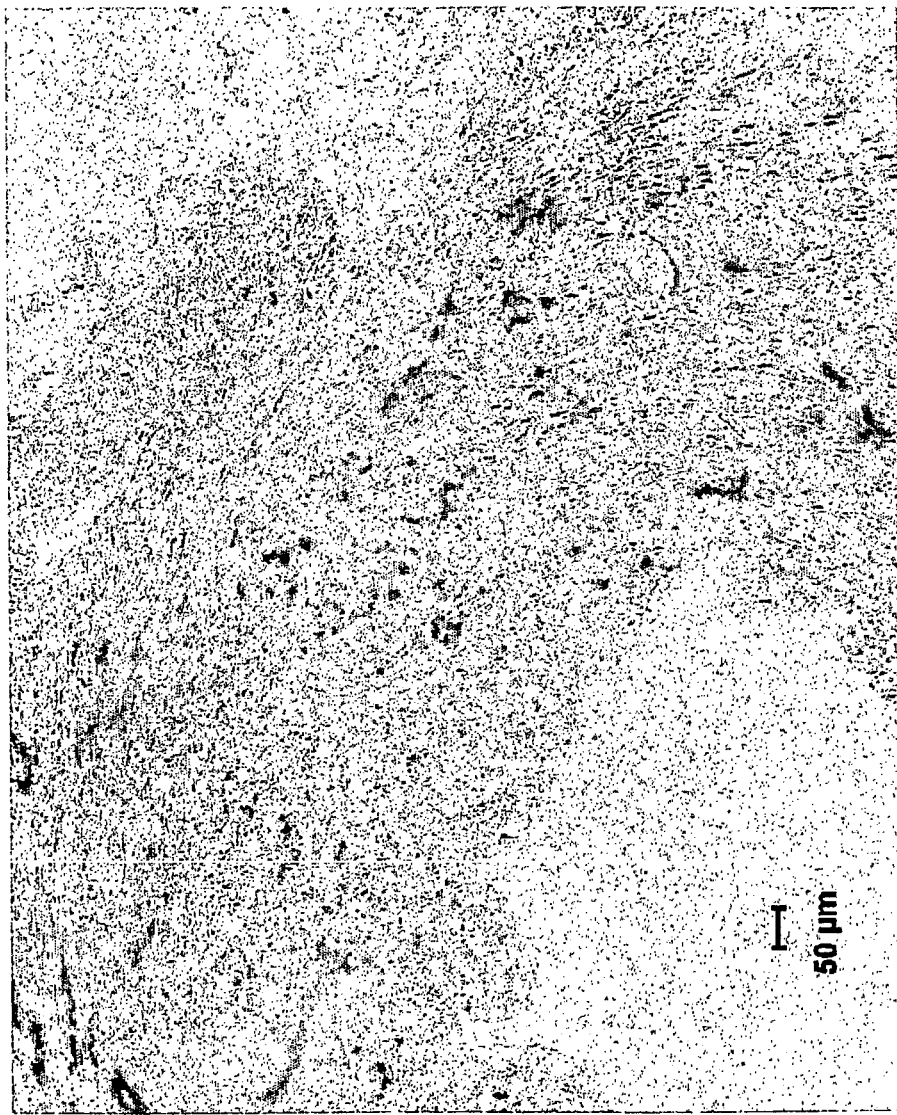
FIG. 14 is a photomicrograph showing β-galactosidase staining of a section of whole heart injected with $MSC_{vlacZ}$ (shown as a blue dot in the peri-infarct zone).
Figure 15A:
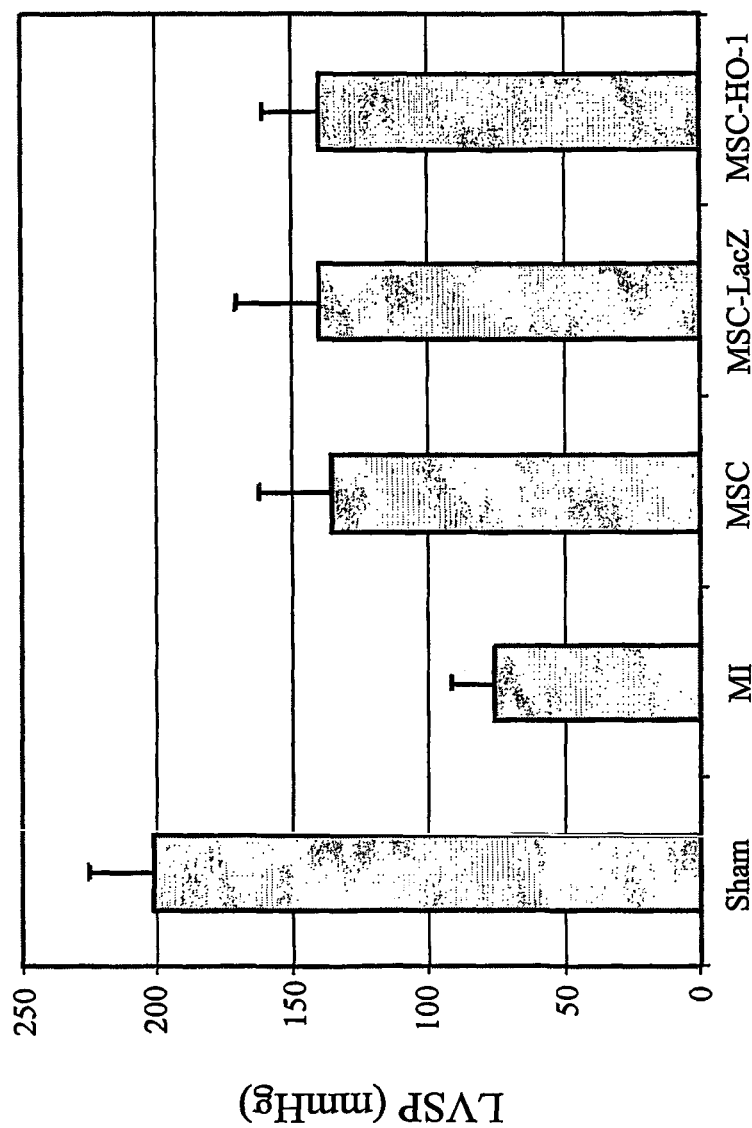
FIGS. 15A-15D show that implantation of MSCs improves left ventricular function. Both LV systolic performance (FIG. 15A) and diastolic performance (FIG. 15B), as assessed by maximum and minimum dP/dt respectively (FIGS. 15C and 15D, respectively), were greatest in the $MSC_{vHO-1}$ group (maximum dP/dt 5717.1±935.4 mmHg/s, minimum dP/dt −4893.3±1435.1 mmHg/s), indicating that both systolic and diastolic functions were best preserved in the $MSC_{vHO-1}$ group after myocardial infarction (maximum dP/dt, P=0.11 versus $MSC_{vlacZ}$, P=0.002 versus MSCs; minimum dP/dt, P=0.01 versus $MSC_{vlacZ}$, P=0.006 versus MSCs). These indicators were better in the $MSC_{vlacZ}$ (maximum dP/dt 4336.0±515.1 mmHg/s P=0.14 versus medium group, minimum dP/dt −3642.1±667.0 mmHg/s P=0.13 versus medium group) and MSCs group (maximum dP/dt 3988.4±450.1 mmHg/s, minimum dP/dt −3559.0±713.0 mmHg/s P=0.21 versus medium group) than in the medium group (maximum dP/dt 3004.6±362.7 mmHg/s, minimum dP/dt −2447.2±621.9 mmHg/s), suggesting that MSCs implantation could preserve cardiac function after myocardial infarction.
Figure 15B:
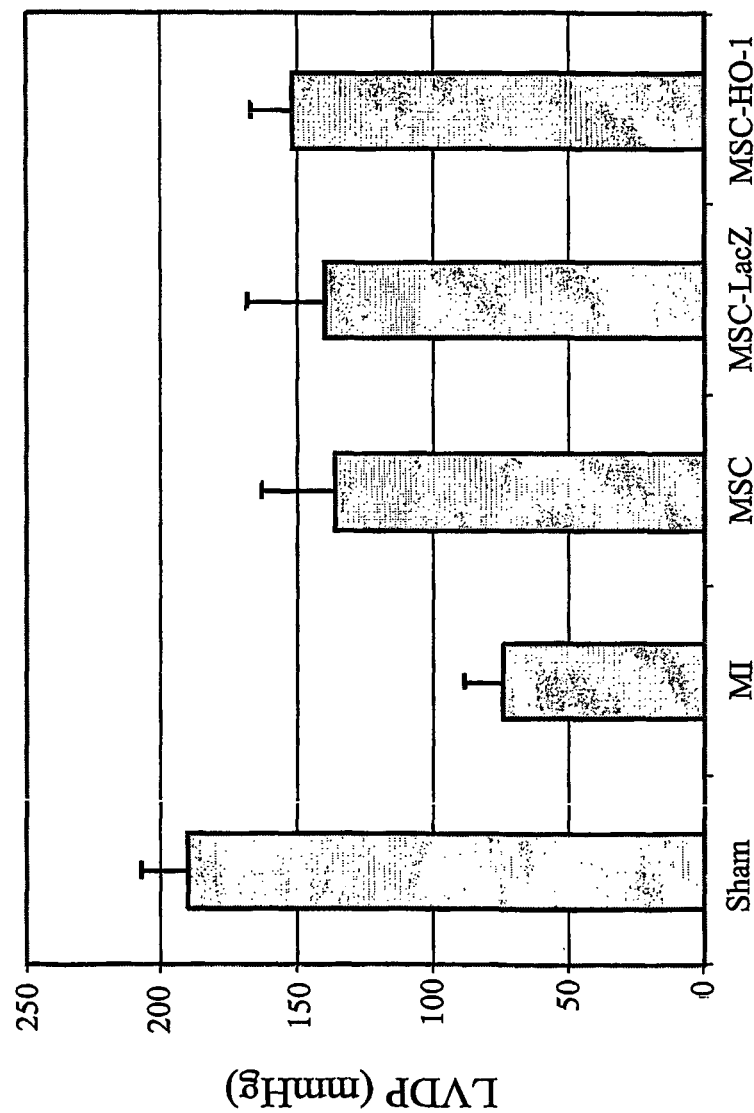
Figure 15C:
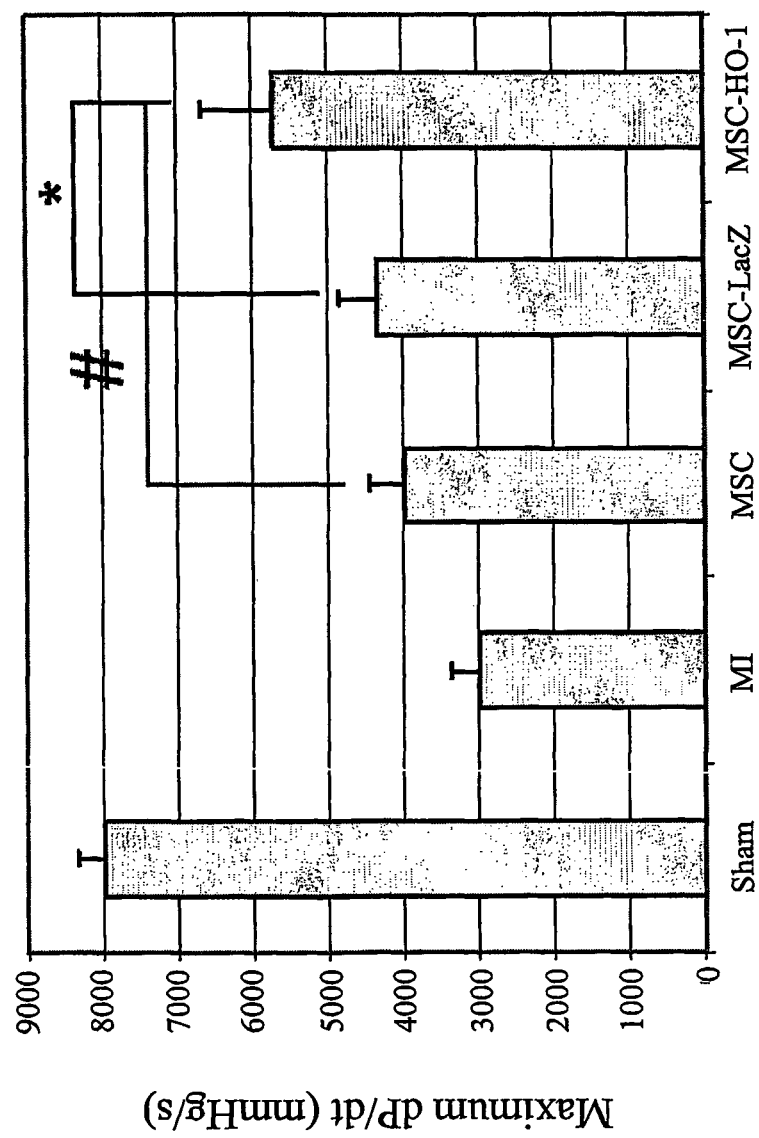
Figure 15D:
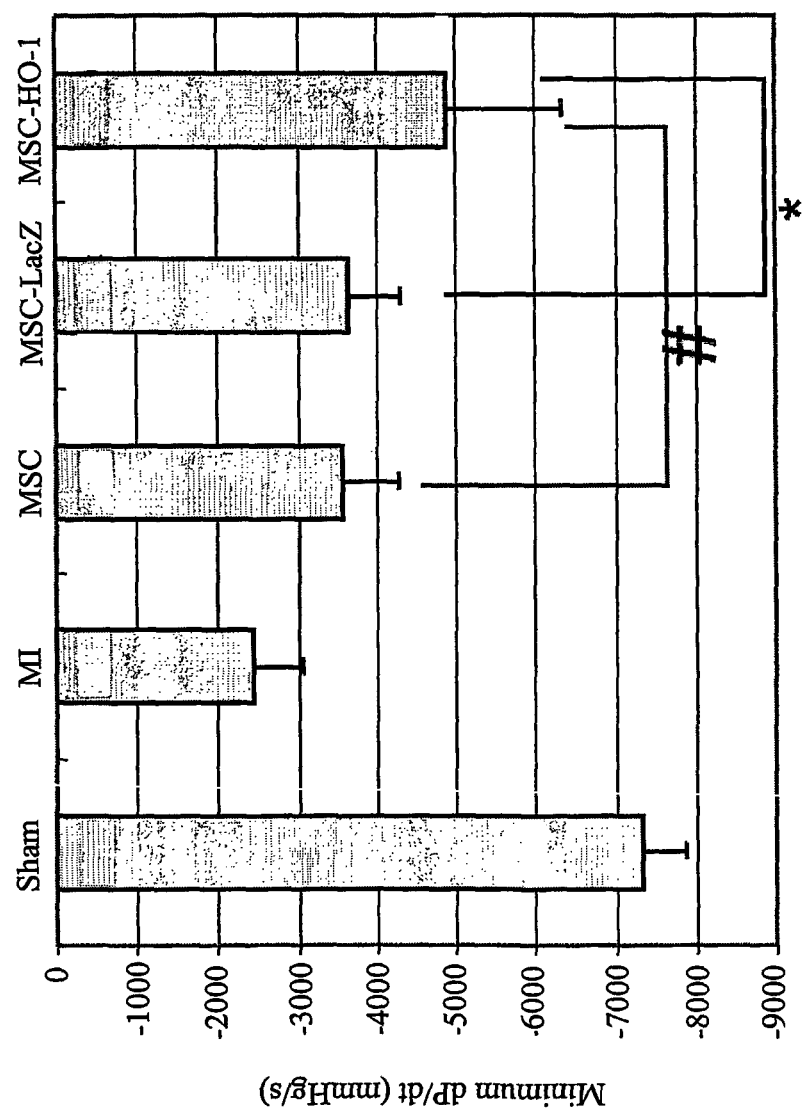

Masson trichrome staining of post-myocardial infarction hearts injected with MSCs showed infiltration of island-like extension of organized cardiac tissue (FIGS. 12A-12D) into the myocardial scar. β-Galactosidase staining of section of whole heart injected with $MSC_{vlacZ}$ show blue dot in the peri-infarct zone (FIG. 14). In ischemic hearts injected with $MSC_{vHO-1}$, groups of cells were positively stained for α-actin and connexin43 at injection sites in the peri-infarct area at 14 days after the transplantation of $MSC_{vHO-1}$ (FIGS. 4A-4C and FIGS. 5A-5C). This suggested that some surviving MSCs had differentiated into myocyte-like cells within the native myocardium. Positive staining was also observed in the $MSC_{vlacZ}$ groups and MSCs groups.

Example 5

Left Ventricular Remodeling and Cardiac Function after MSCs Transplantation

At day 14 after cell transplantation, $MSC_{vHO-1}$ group showed less infarct size than MSC groups in comparison with the medium group (38.9±18.8% versus 60.3±13.8%, p=0.041). Further, infarct wall of left ventricular was thicker in $MSC_{vHO-1}$ group in compared with MSC group (1239.9±174.1 µm versus 979.1±85.6 µm, p=0.036) (FIGS. 12A-12D and FIGS. 13A-13B). Both LV systolic performance and diastolic performance, as assessed by maximum and minimum dP/dt respectively, were greatest in the $MSC_{vHO-1}$ group (maximum dP/dt 5717.1±935.4 mmHg/s, minimum dP/dt −4893.3±1435.1 mmHg/s), indicating that both systolic and diastolic functions were best preserved in the $MSC_{vHO-1}$ group after myocardial infarction (maximum dP/dt, P=0.11 versus $MSC_{vlacZ}$, P=0.002 versus MSCs; minimum dP/dt, P=0.01 versus $MSC_{vlacZ}$, P=0.006 versus MSCs). These indicators were better in the $MSC_{vlacZ}$ (maximum dP/dt 4336.0±515.1 mmHg/s P=0.14 versus medium group, minimum dP/dt −3642.1±667.0 mmHg/s P=P=0.13 versus medium group) and MSCs group (maximum dP/dt 3988.4±450.1 mmHg/s, minimum dP/dt −3559.0±713.0 mmHg/s P=0.21 versus medium group) than in the medium group (maximum dP/dt 3004.6±362.7 mmHg/s, minimum dP/dt −2447.2±621.9 mmHg/s), suggesting that MSCs implantation could preserve cardiac function after myocardial infarction (FIGS. 15A-15D).

Example 6

Vigilant Stem Cell Transplantation in Human Subjects

Marrow isolation: Bone marrow is isolated from the iliac crest of patients with coronary artery disease after informed consent. Mononuclear cells in the bone marrow sample are isolated by Ficoll-density gradient centrifugation. The nucleated cells are centrifuged for 5 minutes at 2000 rpm (447×g), the cell pellet is resuspended, and the cells are adjusted to a concentration of $5 \times 10^7$ nucleated cells per ml in DMEM medium supplemented with 20% FBS and 100 U/ml penicillin G and 100 ug/mg streptomycin). The cells are placed into a 75 cm² coming flask and cultured in a humidified incubator at 37° C. with 5% $CO_2$.

MSC Isolation and Expansion: In the cultures, the medium is replaced every 4 days, keeping the adherent cells and discarding nonadherent cells. Each primary culture is passaged to two new flasks when the MSCs grow to approximately 70% confluence. After a series of passages, homogeneous MSCs devoid of hematopoietic cells are collected and used for cell transfection. MSCs are genetically modified with AAV-based vectors, cloned, expanded, and labeled as in Example 1.

Delivery of Vigilant Cells: Vigilant cells can be delivered (e.g. injected) directly into the peripheral infarct zone for myocardial regeneration, e.g., when MI patients undergo surgical treatment such as coronary artery bypass or interventional treatment such as percutaneous transluminal angioplasty (PTCA). For example, coronary artery bypass grafting (CABG) is performed in a coronary artery disease (CAD) patient. Once all bypass-to-coronary-artery anastomoses are completed, a vigilant cell suspension (eight injections containing autologous vigilant cells in 0.5 mL, total $4 \times 10^8$ cells in 4 mL) is injected into the peri-infarct zone using a 27-gauge needle. The operation is completed as is standard in the art.

The present inventors have demonstrated that transplantation of vigilant HO-1 vector-engineered MSCs can reduce infarct size and improve cardiac function after left coronary artery occlusion. Moreover, it has been shown by the experiments herein that the grafting of MSCs expressing vigilant HO-1 provides advanced benefits in preserving graft MSCs and reducing infarct size. These effects were probably clue to reduced apoptosis in grafted MSCs and host heart. These data show that transplantation of vigilant HO-1-MSCs could be of significant value in treating acute myocardial infarction.

The acute donor cell death that occurs immediately after engraftment is thought to have a major negative impact on the ensuing graft size. It is imperative to identify the basis for the grafted cell death and to develop strategies aimed at limiting the process (Reinlib, L. and Field, L. *Circulation*, 2000, 101: E182-E187). Implanted bone marrow stromal cells seem to be highly sensitive to hypoxic and inflammatory environment in ischemic myocardium. Moreover, majority of myocardial ischemia is characterized by repeated ischemic bouts which will cause ischemic/reperfusion damage to implanted stem cells. So there is only marginal improvement in cardiac function after transplantation of MSCs into infracted porcine heart (Shake, J. G. et al. *Ann. Thorac. Surg.*, 2002, 73:1919-1925). Therapeutic application of MSCs might ultimately require additional interventions to protect grafted MSCs with the ability of anti-ischemia in short-term and anti-ischemic/reperfusion damage in long-term. Accordingly, graft stem cells need to be engineered with beneficial genes to render grafted stem cells resistant to apoptosis, remain viable in ischemic tissue, and enhance cardiac repair after transplantation into the ischemic myocardium.

Exploiting cell growth and death regulatory factors to enhance proliferation or confer apoptosis resistance to donor cells is a potential way to improve cell transplant efficiency. Mangi et al. (Mangi, A. A. et al. *Nat. Med.*, 2003, 9:1195-1201) demonstrated that a direct intramuscular injection of $5 \times 10^6$ Aktengineered MSCs improved the function of infracted rat hearts. Akt is a powerful survival signal in many systems. However, the overall application may be affected by constitutively active Akt gene which increases the risk of tumorigenesis. With an increased understanding of the key role of heme oxygenase-1 (HO-1) in the adaptation and defense against cellular stress, HO-1 is a good candidate for providing a useful approach for cellular protection through anti-inflammation and anti-apoptosis mechanism. A system for modulating tissue physiology has been developed which is based on an oxygen dependent degradation domain (ODD) from the hypoxia inducible factor-1-alpha (HIF1-α) which can sense ischemia and switch on cardioprotective gene. This gene system was employed to genetically manipulated graft MSCs, which improve autologous survival in local ischemic environment because cells integrated with vectors containing a gene switch/biosensor and a gene amplification system to prevent or reverse tissue damage caused by disease. This system contains two vectors: A sensor vector contains a CMV promoter linked to a sequence encoding an oxygen-sensitive chimeric transactivator containing a GAL4 DBD, an oxygen-dependent degradation domain, and a p65 AD. An effector vector contains a cardioprotective gene-hHO-1 linked to a GAL4 UAS. The first vector expresses the chimeric transactivator specifically in the graft MSCs in response to hypoxia, the transactivator binds to the GAL4 UAS in the effector rAAV vector. Binding of the transactivator to the UAS results in the expression of the hHO-1 gene. Accordingly, Grafted MSCs modified in this manner might more efficiently supplement the function of weakened regenerated myocardium than unmodified cells because the vectors allow transgene expression in the regenerated tissue from vigilant cells to be regulated in response to a physiological signal, to be switched on or off, and to provide high enough levels to effect a desired result, e.g., prevention or reversal of cardiomyocyte damage. In this study, it is demonstrated that hypoxic treatment of engineered MSCs activates vigilant vector system expressing hHO-1 in MSCs and improves their survival in cell culture; Furthermore, it enhance their survival after engraftment to the ischemic myocardium.

In the early phase of myocardial ischemia, this strategy may salvage ischemic host myocardium through HO-1 as mediated by anti-inflammatory and anti-apoptosis protection. In the late phase, regenerating muscle from survival MSCs could play an additional role in limiting infarct growth and improving infracted heart function. Improving donor cell viability can not only limit infarct size, but to secrete proteins encoding cardioprotective activity to benefit a diseased heart (Koh, G. Y. et al. *J. Clin. Invest.*, 1995, 95:114-121).

Graft MSCs require vasculature to provide blood supply for their survival. It has been demonstrated that implanted MSCs can differentiate into endothelial phenotype and enhance vascular density as early as day 5 after implantation in rat myocardial infarction model (Davani, S. et al. *Circulation*, 2003, 108 (Suppl. 1):II253-II258). This short time window enable the use of non-viral vectors. The use of TfPEI has been shown to result in a transient and high-efficiency transfection, with little cell toxicity (Ogris, M. et al. *Gene Ther*, 1998-5:1425-1433. Kircheis, R. et al. *Gene Ther.*, 2001, 8:28-40). Nonviral vectors is safe and efficient to protect graft MSCs from short-term ischemic damage, however, long-term protection from ischemia/reperfusion damage may be problematic if these systems do not integrate into MSCs genome. Viral vectors such as adeno-associated virus and lentivirus can afford long-lasting protective gene expression in infected MSCs. Therefore, new cardiomyocyte differentiated from engineering MSCs to express hypoxia inducible HO-1 would have a capability of self-protective in face of further repetitive ischemia.

In conclusion, the efficacy of the implantation of vigilant HO-1-engineering MSCs into a mouse model of myocardial infarction was demonstrated. It was shown that engrafted MSCs acquired auto-protective ability in short-term study. This pre-treatment leads to higher survival of grafting stem cell and is associated with the improvement of heart function. So cellular cardiomyoplasty with pre-treated MSCs might be a viable way to protect graft stem cells.

These data demonstrate that vigilant HO-1 pretreatment can improve grafting MSCs survival and improve contraction. Additional studies can be conducted to evaluate whether engineered MSCs-derived regenerated myocardium possess more antiischemic/reperfusion ability than host cardiomyocytes. To facilitate long-term studies, viral vectors can be used to incorporate the vigilant HO-1 gene into the chromosomes of the grafting MSCs. As more knowledge regarding the engineering of MSCs for survival and differentiation in vivo in the long-term is gained, cellular therapy can be made more successful in treatment of ischemic heart disease.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

All patents, patent applications, provisional applications, and publications referred to or cited herein are incorporated by reference in their entirety, including all figures and tables to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A genetically modified stem or progenitor cell comprising:
    (a) a first exogenous polynucleotide comprising a gene switch/biosensor operatively linked to a promoter, wherein said gene switch/biosensor encodes an oxygen-sensitive chimeric transactivator; and
    (b) a second exogenous polynucleotide comprising a gene amplification system, wherein said gene amplification system comprises a nucleic acid sequence encoding a therapeutic product, wherein said therapeutic product is heme oxygenase-1 (HO-1);
    wherein said cell comprises a non-viral vector comprising said first and second exogenous polynucleotides.

2. The cell of claim 1, wherein said gene amplification system further comprises a GAL4 upstream activating sequence (UAS) linked to said nucleic acid sequence encoding said therapeutic product.

3. The cell of claim 2, wherein said physiological stimulus is a signal associated with a pathological condition, and wherein said chimeric transactivator of said first exogenous polynucleotide binds to said GAL4 UAS of the second exogenous polynucleotide in response to the signal associated with the pathological condition, resulting in expression of the therapeutic nucleic acid sequence encoding the therapeutic product.

4. The cell of claim 3, wherein said signal is hypoxia associated with ischemia.

5. The cell of claim 1, wherein said gene switch/biosensor comprises an operatively linked promoter, wherein said oxygen-sensitive chimeric transactivator comprises a GAL4 DNA-binding domain (DBD), an oxygen-dependent degradation domain (ODD), and a p65 activation domain (p65AD); and wherein said nucleic acid sequence encoding a therapeutic product comprises a cardioprotective gene linked to a GAL4 upstream activating sequence (UAS).

6. The cell of claim 1, wherein said cell is a pluripotent or totipotent stem cell.

7. The cell of claim 1, wherein said cell is selected from the group consisting of a hematopoietic stem cell, a mesenchymal stem cell (MSC), a muscle derived stem cell, and a bone marrow mesenchymal progenitor cell (MPC).

8. The cell of claim 1, wherein said therapeutic product is a polypeptide that is heterologous to said cell.

9. The cell of claim 1, wherein said therapeutic product is a polypeptide that is endogenous to said cell.

10. A modified mammalian tissue, wherein said tissue comprises a genetically modified mammalian stem or progenitor cell, wherein said cell comprises:
   (a) a first exogenous polynucleotide comprising a gene switch/biosensor operatively linked to a promoter, wherein said gene switch/biosensor encodes an oxygen-sensitive chimeric transactivator; and
   (b) a second exogenous polynucleotide comprising a gene amplification system, wherein said gene amplification system comprises a nucleic acid sequence encoding a therapeutic product, wherein said therapeutic product is heme oxygenase-1 (HO-1);
   wherein said cell comprises a non-viral vector comprising said first and second exogenous polynucleotides.

11. The tissue of claim 10, wherein said tissue is human tissue and said cell is a human cell.

12. The tissue of claim 10, wherein said cell is autologous to said tissue.

13. The tissue of claim 10, wherein said tissue is myocardium, mesenchymal tissue, pancreatic tissue, liver tissue, or brain tissue.

14. The tissue of claim 10, wherein said cell is a hematopoietic stem cell, a mesenchymal stem cell (MSC), a muscle derived stem cell, or a bone marrow mesenchymal progenitor cell (MPC).

15. The cell of claim 1, wherein said promoter is a cytomegalovirus (CMV) promoter.

16. The tissue of claim 10, wherein said promoter is a cytomegalovirus (CMV) promoter.

* * * * *

UNITED STATES PATENT AND TRADEMARK OFFICE
CERTIFICATE OF CORRECTION

PATENT NO. : 9,040,676 B2
APPLICATION NO. : 10/567298
DATED : May 26, 2015
INVENTOR(S) : M. Ian Phillips and Yao Liang Tang It is certified that error appears in the above-identified patent and that said Letters Patent is hereby corrected as shown below:

In the specification

Column 1,
Line 23, "may have has certain" should read --has certain--.

Column 3,
Line 59, "$MSC_{vHO-1}$" should read --$MSC_{VHO-1}$--.
Line 67, "$MSC_{vHO-1}$" should read --$MSC_{VHO-1}$--.

Column 4,
Line 45, "979.1±485.61 μm," should read --979.1±85.6 μm,--.

Column 7,
Line 40, "Littre," should read --Littré,--.

Column 18,
Line 9, "$PO_2$" should read --$pO_2$--.

Signed and Sealed this
Fifth Day of January, 2016

Michelle K. Lee
*Director of the United States Patent and Trademark Office*